(12) United States Patent
Jensen et al.

(10) Patent No.: US 8,026,214 B2
(45) Date of Patent: Sep. 27, 2011

(54) LIQUID, AQUEOUS PHARMACEUTICAL COMPOSITIONS OF FACTOR VII POLYPEPTIDES

(75) Inventors: Michael Bech Jensen, Allerød (DK); Anders Klarskov Petersen, Nærum (DK); Andrew Neil Bowler, Gentofte (DK)

(73) Assignee: Novo Nordisk Health Care AG, Zurich (CH)

( * ) Notice: Subject to any disclaimer, the term of this patent is extended or adjusted under 35 U.S.C. 154(b) by 0 days.

(21) Appl. No.: 12/617,471

(22) Filed: Nov. 12, 2009

(65) Prior Publication Data
US 2010/0056453 A1    Mar. 4, 2010

Related U.S. Application Data

(63) Continuation of application No. 11/353,335, filed on Feb. 14, 2006, now Pat. No. 7,732,405, which is a continuation of application No. PCT/DK2004/000537, filed on Aug. 12, 2004.

(60) Provisional application No. 60/496,443, filed on Aug. 20, 2003.

(30) Foreign Application Priority Data

Aug. 14, 2003  (DK) .............................. 2003 01161
Mar. 18, 2004  (WO) ............... PCT/DK2004/000181

(51) Int. Cl.
*A61K 38/36* (2006.01)
*A61K 31/17* (2006.01)

(52) U.S. Cl. .......... 514/12; 514/597; 530/350; 530/384; 424/9.1

(58) Field of Classification Search .................. 514/12, 514/597; 530/384, 350; 424/9.1
See application file for complete search history.

(56) References Cited

U.S. PATENT DOCUMENTS

| | | |
|---|---|---|
| 4,297,344 A | 10/1981 | Schwinn et al. |
| 4,382,083 A | 5/1983 | Thomas |
| 4,404,132 A | 9/1983 | Mitra |
| 4,495,278 A | 1/1985 | Thomas |
| 4,784,950 A | 11/1988 | Hagen et al. |
| 4,956,386 A | 9/1990 | McLoughlin et al. |
| 5,180,583 A | 1/1993 | Hedner |
| 5,288,629 A | 2/1994 | Berkner |
| 5,399,670 A | 3/1995 | Bhattacharya et al. |
| 5,457,181 A | 10/1995 | Michalski et al. |
| 5,576,291 A | 11/1996 | Curtis et al. |
| 5,649,959 A | 7/1997 | Hannam et al. |
| 5,700,914 A | 12/1997 | Jørgensen et al. |
| 5,750,358 A | 5/1998 | Morrissey |
| 5,770,700 A | 6/1998 | Webb et al. |
| 5,804,420 A | 9/1998 | Chan |
| 5,817,788 A | 10/1998 | Berkner et al. |
| 5,824,780 A | 10/1998 | Curtis et al. |
| 5,830,852 A | 11/1998 | Thatcher et al. |
| 5,831,026 A | 11/1998 | Almstedt et al. |
| 5,833,982 A | 11/1998 | Berkner et al. |
| 5,925,738 A | 7/1999 | Miekka et al. |
| 5,925,739 A | 7/1999 | Spira et al. |
| 5,962,650 A | 10/1999 | Osterberg et al. |
| 5,993,795 A | 11/1999 | Osawa et al. |
| 6,034,222 A | 3/2000 | Fischer et al. |
| 6,183,743 B1 | 2/2001 | Hart et al. |
| 6,228,620 B1 | 5/2001 | Chapman et al. |
| 6,277,828 B1 | 8/2001 | Knepp et al. |
| 6,310,183 B1 | 10/2001 | Johannessen et al. |
| 6,320,029 B1 | 11/2001 | Miekka et al. |
| 6,461,610 B1 | 10/2002 | Kongsbak et al. |
| 6,586,573 B1 | 7/2003 | Besman et al. |
| 6,586,574 B1 | 7/2003 | Hansen |
| 6,599,724 B1 | 7/2003 | Mikaelsson et al. |
| 6,750,053 B1 | 6/2004 | Widrig Opalsky et al. |
| 6,806,063 B2 | 10/2004 | Pedersen et al. |
| 6,825,323 B2 | 11/2004 | Hess |
| 6,833,352 B2 | 12/2004 | Johannessen et al. |
| 6,858,587 B2 | 2/2005 | Sorensen et al. |
| 6,903,069 B2 | 6/2005 | Pingel et al. |
| 6,908,610 B1 | 6/2005 | Sato |
| 7,015,194 B2 | 3/2006 | Kjalke |
| 7,078,479 B2 | 7/2006 | Rojkjaer |
| 7,125,846 B2 | 10/2006 | Rojkjaer |
| 7,173,000 B2 | 2/2007 | Ruf et al. |
| 2001/0031721 A1 | 10/2001 | Webb et al. |
| 2002/0110552 A1 | 8/2002 | Romisch et al. |
| 2002/0115590 A1 | 8/2002 | Johannessen et al. |
| 2003/0082807 A1 | 5/2003 | Wengel |
| 2003/0109446 A1 | 6/2003 | Rojkjaer |

(Continued)

FOREIGN PATENT DOCUMENTS

AU   2003/289742   7/2007

(Continued)

OTHER PUBLICATIONS

Cleland, M.C. et al., Pharm Res. vol. 6(11), pp. 903-918 (1989).
Mannng, J.L. et al., Crit Rev in Thera Drug Carr Sys., vol. 10(4), pp. 307-377 (1993).
Sichler, K. et al., J. Mol. Biol., vol. 322(3), pp. 591-603 (2002).
Wang et al., J. Parenter Sci Technol, vol. 42(10), pp. 4-26 (1988).
Bach et al., 1984, "Immunoaffinity Purification of Bovine Factor VII," Blood 63(2):393-398.
Bajaj et al., 1981, "Isolation and Characterization of Human Factor VII," Journal of Biological Chemistry 256(1):253-259.

(Continued)

*Primary Examiner* — Chih-Min Kam
(74) *Attorney, Agent, or Firm* — Michael J. Brignati

(57) ABSTRACT

The present invention is directed to liquid, aqueous pharmaceutical compositions stabilised against chemical and/or physical degradation containing Factor VII polypeptides, and methods for preparing and using such compositions, as well as vials containing such compositions, and the use of such compositions in the treatment of a Factor VII-responsive syndrome. The main embodiment is represented by a liquid, aqueous pharmaceutical composition comprising at least 0.01 mg/mL of a Factor VII polypeptide (i); a buffering agent (ii) suitable for keeping pH in the range of from about 4.0 to about 9.0; and at least one stabilising agent (iii) comprising a —C(=N—$Z^1$—$R^1$)—NH—$Z^2$—$R^2$ motif, e.g. benzamidine compounds and guanidine compounds such as arginine.

9 Claims, No Drawings

U.S. PATENT DOCUMENTS

| | | | |
|---|---|---|---|
| 2004/0009918 A1 | 1/2004 | Nedergaard et al. |
| 2004/0037893 A1 | 2/2004 | Hansen et al. |
| 2004/0043933 A1 | 3/2004 | Hansen et al. |
| 2005/0266006 A1 | 12/2005 | Rojkjaer |
| 2006/0009376 A1 | 1/2006 | Eibl |
| 2006/0013812 A1 | 1/2006 | Rojkjaer |
| 2006/0063714 A1 | 3/2006 | Jensen et al. |
| 2006/0160720 A1 | 7/2006 | Jensen et al. |
| 2007/0049523 A1 | 3/2007 | Hansen et al. |
| 2009/0075895 A1 | 3/2009 | Nedergaard |
| 2010/0136622 A1 | 6/2010 | Krarup |

FOREIGN PATENT DOCUMENTS

| | | |
|---|---|---|
| CA | 2304396 | 4/1999 |
| CA | 2315309 | 2/2001 |
| DE | 19853033 | 5/2000 |
| EP | 052874 | 6/1982 |
| EP | 225160 | 6/1987 |
| EP | 430200 | 6/1991 |
| EP | 547932 | 6/1993 |
| EP | 765669 | 7/1996 |
| EP | 770625 | 9/1996 |
| EP | 872487 | 10/1998 |
| EP | 952215 | 10/1999 |
| EP | 1232753 | 8/2002 |
| JP | 62-195335 | 8/1987 |
| JP | 3-155797 | 7/1991 |
| JP | 6-504678 | 6/1994 |
| JP | 8-509745 | 10/1996 |
| JP | 11-500408 | 1/1999 |
| JP | 2000-302689 | 10/2000 |
| JP | 2000/513720 | 10/2000 |
| NZ | 336548 | 8/2001 |
| WO | WO 88/00210 | 1/1988 |
| WO | WO 91/10439 | 7/1991 |
| WO | WO 92/15686 | 9/1992 |
| WO | WO 93/00807 | 1/1993 |
| WO | WO 94/05692 | 3/1994 |
| WO | WO 94/22905 | 10/1994 |
| WO | WO 94/26286 | 11/1994 |
| WO | WO 94/27631 | 12/1994 |
| WO | WO 95/28954 | 11/1995 |
| WO | WO 96/12800 | 5/1996 |
| WO | WO 97/14430 | 4/1997 |
| WO | WO 97/19687 | 6/1997 |
| WO | WO 97/26909 | 7/1997 |
| WO | WO 97/47651 | 12/1997 |
| WO | WO 98/12225 | 3/1998 |
| WO | WO 98/22619 | 5/1998 |
| WO | WO 98/48822 | 11/1998 |
| WO | WO 99/02160 | 1/1999 |
| WO | WO 99/49880 | 10/1999 |
| WO | WO 99/66031 | 12/1999 |
| WO | WO 00/20835 | 4/2000 |
| WO | WO 00/48635 | 8/2000 |
| WO | WO 00/72873 | 12/2000 |
| WO | WO 01/03726 | 1/2001 |
| WO | WO 01/12653 | 2/2001 |
| WO | WO 01/17542 | 3/2001 |
| WO | WO 01/17567 | 3/2001 |
| WO | WO 01/17569 | 3/2001 |
| WO | WO 01/58935 | 8/2001 |
| WO | WO 01/82943 | 11/2001 |
| WO | WO 01/83725 | 11/2001 |
| WO | WO 01/85198 | 11/2001 |
| WO | WO 01/85199 | 11/2001 |
| WO | WO 02/17957 | 3/2002 |
| WO | WO 02/22776 | 3/2002 |
| WO | WO 03/002524 | 1/2003 |
| WO | WO 03/007868 | 1/2003 |
| WO | WO 03/055511 | 7/2003 |
| WO | WO 03/055512 | 7/2003 |
| WO | WO 03/092731 | 11/2003 |
| WO | WO 04/000347 | 12/2003 |
| WO | WO 2004/082708 | 9/2004 |
| WO | WO 2004/110469 | 12/2004 |

OTHER PUBLICATIONS

Blajchman, 2001, "Novel platelet products, substitutes and alternatives," Transfusion Clinique et Biologique 8(3):267-271.

Broze et al., 1980, "Purification and Properties of Human Coagulation Factor VII," Journal of Biological Chemistry 255(4):1242-1247.

Brozovic et al., 1971, "Stability of Prothrombin and Factor VII in Freeze-Dried Plasma," Journal of Clinical Pathology 24:690-693.

Cleland et al., 1993, "The Development of Stable Protein Formulations: A Close Look At Protein Aggregation, Deamidation, and Oxidation," Critial Reviews in Therapeutic Drug Carrier Systems 10(4):307-377.

Cooper, 1983, "Biochemistry of Sulfur-Containing Amino Acids," Annual Review of Biochemistry 52:187-222.

Dike et al., 1980, "A Factor VII Concentrate for Therapeutic Use," British Journal of Haematology 45:107-118.

Dombrose et al., 1973, "Evidence for Multiple Molecular Forms of Autoprothrombin C (Factor XA)," Thrombosis Research 3:737-743.

Husi et al., 1999, "Separation of Human Vitamin K-Dependent Coagulation Proteins Using Hydrophobic Interaction Chromatography," Journal of Chromatography B 736:77-88.

Jesty et al., 1974, "Purification of Factor VII From Bovine Plasma," Journal of Biological Chemistry 249(2):509-515.

Klausen, N. K et al., 1995, "Analysis of the Glycoforms of Human Recombinant Factor VIIA by Capillary Electrophoresis and High-Performance Liquid Chromatography" Journal of Chromatography A 718:195-202.

Krarup et al., 2003, "Studies on Coagulation Factor VIIA . . . " Abstracts of Papers—American Chemical Society 225(1-2):201-202, Abstract# : BIOT333.

Krylov, Chief Editor, 2001, Enziklopedia Lekarstv. M., RLS-2001, 468: Encyclopedia of Drugs, p. 468.

English Translation of Krylov, Chief Editor, 2001, Enziklopedia Lekarstv. M., (Encyclopaedia of Medicines/Drugs) RLS-2001, 468; Encyclopedia of Drugs, pp. 468.

Liebman et al., 1985, "Immunoaffinity Purification of Factor IX (Christmas Factor) by Using Conformation-Specific Antibodies Directed Against the Factor IX-Metal Complex," Proceedings of the National Academy of Sciences of the USA 82:3879-3883.

Manning et al., 1989, "Stability of Protein Pharmaceuticals," Pharmaceutical Research 6(11):903-918.

Nemerson et al., 1973, "Activation of a Proteolytic System by a Membrane Lipoprotein: Mechanism of Action of Tissue Factor," Proceedings of the National Academy of Sciences of the USA 70(2):310-314.

Novo Nordisk, 2000, "Koagulationsfaktor VIIA," Lægemiddel Kataloget pp. 893-894 and English Translation.

Novo Nordisk A/S, 1999, NOVOSEVEN(R) Coagulation Factor VIIA (Recombinant) Package Insert.

Novo Nordisk, 1999, "Novoseven Coagulation Factor VIIA (Recombinant)," FDA Article Online pp. 1-24.

O'Brien et al., 1991, "Purification and Characterization of Factor VII 304-GLN: A Variant Molecule With Reduced Activity Isolated From a Clinically Unaffected Male," Blood 78(1):132-140.

PCT/DK2004/000183 International Search Report, dated Jul. 22, 2004.

PCT/DK2004/000181 International Search Report, dated Feb. 9, 2005.

PCT/DK2004/000359 International Search Report dated Oct. 1, 2004.

PCT/DK2003/00419 International Search Report, dated Oct. 20, 2003.

Porter et al., 1984, "Growth Inhibition by Methionine Analog Inhibitors of S-Adenosylmethionine Biosynthesis in the Absence of Polyamine Depletion," Biochemical and Biophysical Research Communications 122(1):350-357.

Rao et al., 1984, "Purification of Human Factor VII Utilizing O-(Diethylaminoethyl)-Sephadex and Sulfopropyl-Sephadex Chromatography," Analytical Biochemistry 136(2):357-361.

Ruiz et al., 2000, "Expression and Purification of Recombinant Rabbit Factor VII," Thrombosis Research 98:203-211.

Tomokiyo et al., 2003, "Large-Scale Production and Properties of Human Plasma-Derived Activated Factor VII Concentrate" Vox Sanguinis 84:54-64.

Wang, 2000, "Lyophilization and Development of Solid Protein Pharmaceuticals," International Journal of Pharmaceutics 203:1-60.
Wang et al., 1988, "Parenteral Drug Association Objectives," Journal of Parenteral Science & Technology 42:2S.
Wells, 1990, "Additivity of Mutational Effects in Proteins," Biochemistry 29(37):8509-8517.
Yan, 1996, "Review of Conformation-Specific Affinity Purification Methods for Plasma Vitamin K-Dependent Proteins," Journal of Molecular Recognition 9:211-218.
EP 765669 English Abstract Apr. 2, 1997.
JP 2000-513720 English Language Machine Translation, published Oct. 17, 2000 (Novo Nordisk A/S).
JP 2000-302689 Machine Translation, Oct. 31, 2000.
JP 11-500408 English Language Machine Translation, published Jan. 12, 1999 (ZymoGenetics and Novo Nordisk A/S).
JP 8-509745 English Language Machine Translation, published Oct. 15, 1996.
JP 6-504678 English Abstract, Mar. 9, 2010.
JP 3-155797 English Abstract, Mar. 7, 1991.
Non-Final Office Action mailed Jul. 2, 2010 in U.S. Appl. No. 12/536,872, filed Aug. 6, 2009 by Jensen et al.
Non-Final Office Action mailed Jul. 7, 2010 in U.S. Appl. No. 12/407,266, filed Mar. 19, 2009 by Hansen et al.
Notice of Allowance mailed Jul. 30, 2010 in U.S. Appl. No. 12/154,088, filed May 20, 2008 by Hansen et al.
Notice of Allowance mailed Apr. 14, 2010 in U.S. Appl. No. 12/154,088, filed May 20, 2008 by Hansen et al.
Notice of Allowance mailed Feb. 1, 2010 in U.S. Appl. No. 12/154,088, filed May 20, 2008 by Hansen et al.
Non-Final Office Action mailed Jul. 29, 2009 in U.S. Appl. No. 12/154,088, filed May 20, 2008 by Hansen et al.
Final Office Action mailed Aug. 26, 2010 in U.S. Appl. No. 11/526,503, filed Sep. 25, 2006 by Jensen et al.
Non-Final Office Action mailed Jan. 4, 2010 in U.S. Appl. No. 11/526,503, filed Sep. 25, 2006 by Jensen et al.
Non-Final Office Action mailed Apr. 6, 2009 in U.S. Appl. No. 11/526,503, filed Sep. 25, 2006 by Jensen et al.
Notice of Abandonment mailed Jul. 14, 2010 in U.S. Appl. No. 11/473,387, filed Jun. 21, 2006 by Hansen et al.
Final Office Action mailed Dec. 30, 2009 in U.S. Appl. No. 11/473,387, filed Jun. 21, 2006 by Hansen et al.
Non-Final Office Action mailed Jan. 29, 2009 in U.S. Appl. No. 11/473,387, filed Jun. 21, 2006 by Hansen et al.
Non-Final Office Action mailed Apr. 8, 2008 in U.S. Appl. No. 11/473,387, filed Jun. 21, 2006 by Hansen et al.
Notice of Abandonment mailed Apr. 7, 2009 in U.S. Appl. No. 11/450,783, filed Jun. 9, 2006 by Hansen et al.
Non-Final Office Action mailed Sep. 18, 2008 in U.S. Appl. No. 11/450,783, filed Jun. 9, 2006 by Hansen et al.
Notice of Allowance mailed Aug. 11, 2009 in U.S. Appl. No. 11/353,335, filed Feb. 14, 2006 by Jensen et al.
Non-Final Office Action mailed Jan. 13, 2009 in U.S. Appl. No. 11/353,335, filed Feb. 14, 2006 by Jensen et al.
Non-Final Office Action mailed Jul. 11, 2008 in U.S. Appl. No. 11/353,335, filed Feb. 14, 2006 by Jensen et al.
Notice of Abandonment mailed Jun. 10, 2008 in U.S. Appl. No. 11/304,429, filed Dec. 15, 2005 by Hansen et al.
Non-Final Office Action mailed Nov. 20, 2007 in U.S. Appl. No. 11/304,429, filed Dec. 15, 2005 by Hansen et al.
Non-Final Office Action mailed Apr. 18, 2007 in U.S. Appl. No. 11/304,429, filed Dec. 15, 2005 by Hansen et al.
Notice of Allowance mailed Apr. 8, 2010 in U.S. Appl. No. 11/304,427, filed Dec. 15, 2005 by Jensen et al.
Notice of Allowance mailed Dec. 15, 2009 in U.S. Appl. No. 11/304,427, filed Dec. 15, 2005 by Jensen et al.
Non-Final Office Action mailed Feb. 6, 2009 in U.S. Appl. No. 11/304,427, filed Dec. 15, 2005 by Jensen et al.
Advisory Action mailed Oct. 23, 2008 in U.S. Appl. No. 11/304,427, filed Dec. 15, 2005 by Jensen et al.
Final Office Action mailed May 2, 2008 in U.S. Appl. No. 11/304,427, filed Dec. 15, 2005 by Jensen et al.
Non-Final Office Action mailed Sep. 11, 2007 in U.S. Appl. No. 11/304,427, filed Dec. 15, 2005 by Jensen et al.
Notice of Abandonment mailed Apr. 17, 2007 in U.S. Appl. No. 11/304,427, filed Dec. 15, 2005 by Jensen et al. and Decision of Petition to Reinstate Granted.
Non-Final Office Action mailed Aug. 27, 2010 in U.S. Appl. No. 11/284,709, filed Nov. 22, 2005 by Jensen et al.
Final Office Action mailed Feb. 19, 2010 in U.S. Appl. No. 11/284,709, filed Nov. 22, 2005 by Jensen et al.
Non-Final Office Action mailed Jun. 4, 2009 in U.S. Appl. No. 11/284,709, filed Nov. 22, 2005 by Jensen et al.
Non-Final Office Action mailed Sep. 25, 2008 in U.S. Appl. No. 11/284,709, filed Nov. 22, 2005 by Jensen et al.
Non-Final Office Action mailed Aug. 6, 2007 in U.S. Appl. No. 11/284,709, filed Nov. 22, 2005 by Jensen et al.
Notice of Allowance mailed May 6, 2010 in U.S. Appl. No. 11/229,428, filed Sep. 15, 2005 by Krarup et al.
Notice of Allowance mailed Jan. 12, 2010 in U.S. Appl. No. 11/229,428, filed Sep. 15, 2005 by Krarup et al.
Notice of Allowance mailed Aug. 28, 2009 in U.S. Appl. No. 11/229,428, filed Sep. 15, 2005 by Krarup et al.
Notice of Allowance mailed May 28, 2009 in U.S. Appl. No. 11/229,428, filed Sep. 15, 2005 by Krarup et al.
Non-Final Office Action mailed Oct. 1, 2008 in U.S. Appl. No. 11/229,428, filed Sep. 15, 2005 by Krarup et al.
Notice of Abandonment mailed Nov. 9, 2009 in U.S. Appl. No. 11/229,427, filed Sep. 15, 2005 by Jensen et al.
Notice of Allowance mailed Jun. 12, 2009 in U.S. Appl. No. 11/229,427, filed Sep. 15, 2005 by Jensen et al.
Advisory Action mailed Apr. 8, 2009 in U.S. Appl. No. 11/229,427, filed Sep. 15, 2005 by Jensen et al.
Final Office Action mailed Jan. 27, 2009 in U.S. Appl. No. 11/229,427, filed Sep. 15, 2005 by Jensen et al.
Non-Final Office Action mailed Jun. 25, 2008 in U.S. Appl. No. 11/229,427, filed Sep. 15, 2005 by Jensen et al.
Non-Final Office Action mailed Nov. 21, 2007 in U.S. Appl. No. 11/229,427, filed Sep. 15, 2005 by Jensen et al.
Notice of Abandonment mailed Oct. 27, 2006 in U.S. Appl. No. 10/609,780, filed Jun. 30, 2003 by Jensen et al.
Non-Final Office Action mailed Mar. 27, 2006 in U.S. Appl. No. 10/609,780, filed Jun. 30, 2003 by Jensen et al.
Notice of Allowance mailed Jun. 22, 2010 in U.S. Appl. No. 10/602,838, filed Jun. 24, 2003 by Hansen et al.
Notice of Allowance mailed Mar. 29, 2010 in U.S. Appl. No. 10/602,838, filed Jun. 24, 2003 by Hansen et al.
Notice of Allowance mailed Dec. 8, 2009 in U.S. Appl. No. 10/602,838, filed Jun. 24, 2003 by Hansen et al.
Final Office Action mailed Jul. 31, 2009 in U.S. Appl. No. 10/602,838, filed Jun. 24, 2003 by Hansen et al.
Non-Final Office Action mailed Feb. 6, 2009 in U.S. Appl. No. 10/602,838, filed Jun. 24, 2003 by Hansen et al.
Advisory Action mailed Sep. 3, 2008 in U.S. Appl. No. 10/602,838, filed Jun. 24, 2003 by Hansen et al.
Final Office Action mailed Feb. 7, 2008 in U.S. Appl. No. 10/602,838, filed Jun. 24, 2003 by Hansen et al.
Non-Final Office Action mailed May 31, 2007 in U.S. Appl. No. 10/602,838, filed Jun. 24, 2003 by Hansen et al.
Advisory Action mailed Mar. 14, 2007 in U.S. Appl. No. 10/602,838, filed Jun. 24, 2003 by Hansen et al.
Final Office Action mailed Oct. 12, 2006 in U.S. Appl. No. 10/602,838, filed Jun. 24, 2003 by Hansen et al.
Non-final Office Action mailed Feb. 7, 2006 in U.S. Appl. No. 10/602,838, filed Jun. 24, 2003 by Hansen et al.
Notice of Abandonment mailed Aug. 2, 2006 in U.S. Appl. No. 10/602,340, filed Jun. 23, 2003 by Hansen et al.
Notice of Abandonment mailed Jan. 5, 2009 in U.S. Appl. No. 10/427,395, filed May 1, 2003 by Nedergaard et al.
Non-Final Office Action mailed May 30, 2008 in U.S. Appl. No. 10/427,395, filed May 1, 2003 by Nedergaard et al.
Advisory Action mailed Aug. 3, 2007 in U.S. Appl. No. 10/427,395, filed May 1, 2003 by Nedergaard et al.
Final Office Action mailed Mar. 19, 2007 in U.S. Appl. No. 10/427,395, filed May 1, 2003 by Nedergaard et al.
Non-Final Office Action mailed Jun. 14, 2006 in U.S. Appl. No. 10/427,395, filed May 1, 2003 by Nedergaard et al.

LIQUID, AQUEOUS PHARMACEUTICAL COMPOSITIONS OF FACTOR VII POLYPEPTIDES

CROSS-REFERENCE TO RELATED PATENT APPLICATIONS

This patent application is a continuation of U.S. application Ser. No. 11/353,335, filed Feb. 14, 2006, now U.S. Pat. No. 7,732,405, which is a continuation (filed under 35 USC §120) of International Patent Application PCT/DK2004/000537 (published as WO 2005/016365), filed Aug. 12, 2004, which designated the US, and further claims the benefit of priority to U.S. Provisional Patent Application 60/496,443, filed Aug. 20, 2003; Danish Patent Application PA 2003 01161, filed Aug. 14, 2003; and International Patent Application PCT/DK04/000181, filed Mar. 18, 2004 under 35 USC §119, the entirety of each of which is hereby incorporated by reference.

FIELD OF THE INVENTION

The present invention is directed to liquid, aqueous pharmaceutical compositions containing Factor VII polypeptides, and methods for preparing and using such compositions, as well as containers containing such compositions, and the use of such compositions in the treatment of a Factor VII-responsive syndrome. More particularly, the invention relates to liquid compositions stabilised against chemical and/or physical degradation.

BACKGROUND OF THE INVENTION

A variety of Factors involved in the blood clotting process have been identified, including Factor VII (FVII), a plasma glycoprotein. Coagulation is initiated by the formation of a complex between Tissue Factor (TF) being exposed to the circulating blood following an injury to the vessel wall, and FVIIa which is present in the circulation in an amount corresponding to about 1% of the total FVII protein mass. FVII exists in plasma mainly as a single-chain zymogen which is cleaved by FXa into its two-chain, activated form, FVIIa. Recombinant activated Factor VIIa (rFVIIa) has been developed as a pro-haemostatic agent. The administration of rFVIIa offers a rapid and highly effective pro-haemostatic response in haemophilic subjects with bleedings, who cannot be treated with other coagulation Factor products due to antibody formation. Also bleeding in subjects with Factor VII deficiency or subjects having a normal coagulation system but experiencing excessive bleeding can be treated successfully with FVIIa.

It is desirable to have administration forms of Factor VIIa suitable for both storage and for delivery. Ideally, the drug product is stored and administered as a liquid. Alternatively, the drug product is lyophilized, i.e. freeze-dried, and then reconstituted by adding a suitable diluent prior to patient use. Ideally, the drug product has sufficient stability to be kept in long-term storage, i.e. more than six months.

The decision to either maintain the finished drug product as a liquid or to freeze-dry it is usually based on the stability of the protein drug in those forms. Protein stability can be affected inter alia by such factors as ionic strength, pH, temperature, repeated cycles of freeze/thaw, and exposures to shear forces. Active protein may be lost as a result of physical instabilities, including denaturation and aggregation (both soluble and insoluble aggregate formation), as well as chemical instabilities, including, for example, hydrolysis, deamidation, and oxidation, to name just a few. For a general review of the stability of protein pharmaceuticals, see, for example, Manning, et al., Pharmaceutical Research 6:903-918 (1989).

While the possible occurrence of protein instabilities is widely appreciated, it is impossible to predict particular instability problems of a particular protein. Any of these instabilities can result in the formation of a protein by-product, or derivative, having lowered activity, increased toxicity, and/or increased immunogenicity. Indeed, protein precipitation may lead to thrombosis, non-homogeneity of dosage form and amount, as well as clogged syringes. Furthermore, post-translational modifications such as, for example, gamma carboxylation of certain glutamic acid residues in the N-terminus and addition of carbohydrate side chains provide potential sites that may be susceptible to modification upon storage. Also, specific to Factor VIIa, being a serine protease, fragmentation due to autocatalysis may occur (enzymatic degradation). Thus, the safety and efficacy of any composition of a protein is directly related to its stability. Maintaining stability in a liquid form is generally different from maintaining stability in a lyophilized form because of highly increased potential for molecular motion and thereby increased probability of molecular interactions. Maintaining stability in a concentrated form is also different from the above, because of the propensity for aggregate formation at increased protein concentrations.

When developing a liquid composition, many factors are taken into consideration. Short-term, i.e. less than six months, liquid stability generally depends on avoiding gross structural changes, such as denaturation and aggregation. These processes are described in the literature for a number of proteins, and many examples of stabilizing agents exist. It is well-known that an agent effective in stabilizing one protein actually acts to destabilize another. Once the protein has been stabilized against gross structural changes, developing a liquid composition for long-term stability (e.g., greater than six months) depends on further stabilizing the protein from types of degradation specific to that protein. More specific types of degradation may include, for example, disulfide bond scrambling, oxidation of certain residues, deamidation, cyclization. Although it is not always possible to pinpoint the individual degradation species, assays are developed to monitor subtle changes so as to monitor the ability of specific excipients to uniquely stabilize the protein of interest.

It is desirable that the pH of the composition is in a physiologically suitable range upon injection/infusion, otherwise pain and discomfort for the patient may result.

For a general review of protein compositions, see, for example, Cleland et al.: The development of stable protein compositions: A closer look at protein aggregation, deamidation and oxidation, Critical Reviews in Therapeutic Drug Carrier Systems 1993, 10(4): 307-377; and Wang et al., Parenteral compositions of proteins and peptides: Stability and stabilizers, Journal of Parenteral Science and Technology 1988 (Supplement), 42 (2S).

Factor VIIa undergoes several degradative pathways, especially aggregation (dimerisation), oxidation, and autolytic cleavage (clipping of the peptide backbone or "heavy chain degradation"). Furthermore, precipitation may occur. Many of these reactions can be slowed significantly by removal of water from the protein. However, the development of an aqueous composition for Factor VIIa has the advantages of eliminating reconstitution errors, thereby increasing dosing accuracy, as well as simplifying the use of the product clinically, thereby increasing patient compliance. Ideally, compositions of Factor VIIa should be stable for more than 6 months over a wide range of protein concentrations. This allows for flexibility in methods of administration. Generally, more highly concentrated forms allow for the administration of lower volumes, which is highly desirable from the patients' point of view. Liquid compositions can have many advantages over freeze-dried products with regard to ease of administration and use.

Today, the only commercially available, recombinantly-made FVII polypeptide composition is a freeze-dried Factor FVIIa product which is reconstituted before use; it contains a relatively low Factor VIIa concentration, e.g., about 0.6 mg/mL. A vial (1.2 mg) of NovoSeven® (Novo Nordisk A/S, Denmark) contains 1.2 mg recombinant human Factor VIIa, 5.84 mg NaCl, 2.94 mg $CaCl_2$, $2H_2O$, 2.64 mg glycylglycine (GlyGly), 0.14 mg polysorbate 80, and 60.0 mg mannitol; it is reconstituted to pH 5.5 by 2.0 mL water for injection (WFI). When reconstituted, the protein solution is stable for use for 24 hours. Thus, no liquid ready-for-use- or concentrated Factor VII products are currently commercially available.

Accordingly, it is an objective of this invention to provide a liquid, aqueous Factor VII polypeptide pharmaceutical composition which provides acceptable control of chemical and/or physical degradation products such as enzymatic degradation or autocatalysis products.

SUMMARY OF THE INVENTION

The present inventors have discovered that Factor VII or analogues thereof ("Factor VII polypeptides"), when formulated as liquid, aqueous pharmaceutical compositions together with at least one stabilising agent (iii) comprising a —C(=N—$Z^1$—$R^1$)—NH—$Z^2$—$R^2$ motif exhibit improved stability and thereby allow for prolonged storage before actual use.

Thus, one aspect of the present invention relates to a liquid, aqueous pharmaceutical composition comprising
at least 0.01 mg/mL of a Factor VII polypeptide (i);
a buffering agent (ii) suitable for keeping pH in the range of from about 4.0 to about 9.0; and
at least one stabilising agent (iii) comprising a —C(=N—$Z^1$—$R^1$)—NH—$Z^2$—$R^2$ motif, wherein
$Z^1$ and $Z^2$ independently are selected from the group consisting of —O—, —S—, —$NR^H$— and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or
$Z^2$ and $R^2$ are as defined above and —C=N—$Z^1$—$R^1$ forms part of a heterocyclic ring, or
$Z^1$ and $R^1$ are as defined above and —C—NH—$Z^2$—$R^2$ forms part of a heterocyclic ring, or
—C(=N—$Z^1$—$R^1$)—NH—$Z^2$—$R^2$ forms a heterocyclic ring wherein —$Z^1$—$R^1$-$R^2$—$Z^2$— is a biradical.

A second aspect of the present invention relates to a method for preparing a liquid, aqueous pharmaceutical composition of a Factor VII polypeptide, comprising the step of providing the Factor VII polypeptide (i) at a concentration of at least 0.01 mg/mL in a solution comprising a buffering agent (ii) suitable for keeping pH in the range of from about 4.0 to about 9.0; and at least one stabilising agent (iii) comprising a —C(=N—$Z^1$—$R^1$)—NH—$Z^2$—$R^2$ motif, wherein
$Z^1$ and $Z^2$ independently are selected from the group consisting of —O—, —S—, —$NR^H$— and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or
$Z^2$ and $R^2$ are as defined above and —C=N—$Z^1$—$R^1$ forms part of a heterocyclic ring, or
$Z^1$ and $R^1$ are as defined above and —C—NH—$Z^2$—$R^2$ forms part of a heterocyclic ring, or
—C(=N—$Z^1$—$R^1$)—NH—$Z^2$—$R^2$ forms a heterocyclic ring wherein —$Z^1$—$R^1$-$R^2$—$Z^2$— is a biradical.

A third aspect of the present invention relates to the liquid, aqueous pharmaceutical composition for use as a medicament.

A fourth aspect of the present invention relates to the use of the liquid, aqueous pharmaceutical composition for the preparation of a medicament for treating a Factor VII-responsive syndrome.

A fifth aspect of the present invention relates to a method for treating a Factor VII-responsive syndrome, the method comprising administering to a subject in need thereof an effective amount of the liquid, aqueous pharmaceutical composition.

A sixth aspect of the present invention relates to an air-tight container containing the liquid, aqueous pharmaceutical composition and optionally an inert gas.

DETAILED DESCRIPTION OF THE INVENTION

As mentioned above, the present invention resides in the development of a novel stabilised liquid, aqueous pharmaceutical composition comprising a Factor VII polypeptide. More specifically, the liquid, aqueous pharmaceutical composition comprises
at least 0.01 mg/mL of a Factor VII polypeptide (i);
a buffering agent (ii) suitable for keeping pH in the range of from about 4.0 to about 9.0; and
at least one stabilising agent (iii) comprising a —C(=N—$Z^1$—$R^1$)—NH—$Z^2$—$R^2$ motif, wherein
$Z^1$ and $Z^2$ independently are selected from the group consisting of —O—, —S—, —$NR^H$— and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or
$Z^2$ and $R^2$ are as defined above and —C=N—$Z^1$—$R^1$ forms part of a heterocyclic ring, or
$Z^1$ and $R^1$ are as defined above and —C—NH—$Z^2$—$R^2$ forms part of a heterocyclic ring, or
—C(=N—$Z^1$—$R^1$)—NH—$Z^2$—$R^2$ forms a heterocyclic ring wherein —$Z^1$—$R^1$-$R^2$—$Z^2$— is a biradical.

The term "$C_{1-6}$-alkyl" is intended to encompass acyclic and cyclic saturated hydrocarbon residues which have 1-6 carbon atoms and which can be linear or branched. Particular examples are methyl, ethyl, n-propyl, isopropyl, cyclopropyl, n-butyl, isobutyl, sec-butyl, tert-butyl, cyclopropylmethyl, n-pentyl, isopentyl, n-hexyl, etc. Similarly, the term "$C_{1-4}$-alkyl" encompasses acyclic and cyclic saturated hydrocarbon residues which have 1-4 carbon atoms and which can be linear or branched.

Similarly, the term "$C_{2-6}$-alkenyl" is intended to encompass acyclic and cyclic hydrocarbon residues which have 2-6 carbon atoms and comprise one unsaturated bond, which can be linear or branched. Examples of $C_{2-6}$-alkenyl groups are vinyl, allyl, but 1 en 1-yl, but-2-en-1-yl, pent-1-en-1-yl, and hex-1-en-1-yl.

The term "optionally substituted" in connection with $C_{1-6}$-alkyl and $C_{2-6}$-alkenyl groups is intended to denote that the group in question may be substituted one or several times, preferably 1-3 times, with group(s) selected from the group consisting of hydroxy, $C_{1-6}$-alkoxy (i.e. $C_{1-6}$-alkyl-oxy), $C_{2-6}$-alkenyloxy, oxo (forming a keto or aldehyde functionality), aryl, aryloxy, arylcarbonyl, heterocyclyl, heterocyclyloxy, heterocyclylcarbonyl, amino, mono- and di($C_{1-6}$-alkyl) amino, halogen, where any aryl and heterocyclyl may be substituted as specifically described below for optionally substituted aryl and heterocyclyl.

"Halogen" includes fluoro, chloro, bromo, and iodo.

When used herein, the term "aryl" is intended to denote a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heterocyclyl" is intended to denote a saturated, partially unsaturated, partially aromatic or fully aromatic carbocyclic ring or ring system where one or more of the carbon atoms have been replaced with heteroatoms, e.g. nitrogen (=N— or —NH), sulphur (—S—), and/or oxygen (—O—) atoms. Examples of such heterocyclyl groups are oxazolyl, oxazolinyl, oxazolidinyl, isoxazolyl, isoxazolinyl, isoxazolidinyl, oxadiazolyl, oxadiazolinyl, oxadiazolidinyl, thiazolyl, iso-thiazolyl, pyrrolyl, pyrrolinyl, pyrrolidinyl, imidazolyl, imidazolinyl, imidazolidinyl, pyrazolyl, pyridinyl, pyrazinyl, pyridazinyl, piperidinyl, coumaryl, furyl, quinolyl, benzothiazolyl, benzotriazolyl, benzodiazolyl, benzoxozolyl, diazolyl, diazolinyl, diazolidinyl, triazolyl, triazolinyl, triazolidinyl, tetrazol, etc. Preferred heterocyclyl groups are 5-, 6- or 7-membered monocyclic groups such as isoxazolyl, isoxazolinyl, oxadiazolyl, oxadiazolinyl, pyrrolyl, pyrrolinyl, diazolyl, diazolinyl, triazolyl, triazolinyl, imidazolyl, imidazolinyl, etc.

The term "heterocyclic ring" is intended to mean a ring corresponding to those defined under "heterocyclyl".

In connection with the terms "aryl", "heterocyclyl" and "heterocyclic ring", the term "optionally substituted" is intended to denote that the group in question may be substituted one or several times, preferably 1-3 times, with group(s) selected from hydroxy (which when present in an enol system may be represented in the tautomeric keto form), $C_{1-6}$-alkyl, $C_{2-6}$-alkenyl, phenyl, benzyl, $C_{1-6}$-alkoxy, oxo (which may be represented in the tautomeric enol form), carboxy, $C_{1-6}$-alkoxycarbonyl, $C_{1-6}$-alkylcarbonyl, amino, mono- and di($C_{1-6}$-alkyl)amino, dihalogen-$C_{1-4}$-alkyl, trihalogen-$C_{1-4}$-alkyl, and halogen. The most typical examples of substituents are hydroxyl, $C_{1-4}$-alkyl, phenyl, benzyl, $C_{1-4}$-alkoxy, oxo, amino, mono- and dimethylamino and halogen.

Besides the fact that $R^1$ and $R^2$ independently can be selected from the group consisting of hydrogen, optionally substituted $C_{1-6}$-alkyl, optionally substituted $C_{2-6}$-alkenyl, optionally substituted aryl, optionally substituted heterocyclyl, it is also possible that a part of the —C(=N—$Z^1$—$R^1$)—NH—$Z^2$—$R^2$ motif may be part of a heterocyclic ring, while the other part of the motif has the meaning defined for $Z^1$, $Z^2$, $R^1$ and $R^2$, respectively. In some interesting embodiments, —C=N—$Z^1$—$R^1$ may form part of a heterocyclic ring selected from the group consisting of a 1,2-diazole ring, an isoxazole ring, a 1,2,4-triazole ring, and a 1,2,4-oxadiazole ring, or —C—NH—$Z^2$—$R^2$ may form part of a heterocyclic ring selected from the group consisting of a 1,2-diazoline ring, an isoxazoline ring, a 1,2,4-triazoline ring, and a 1,2,4-oxadiazoline ring. Such heterocyclic rings may be substituted as described above.

In some embodiments, at least one of $R^1$ and $R^2$ is hydrogen, e.g. both are hydrogen. Further, in some embodiment, which may be combined with the embodiments mentioned before, at least one of $Z^1$ and $Z^2$ is a single bond, e.g. both are a single bond. In special embodiments, $R^1$ and $R^2$ are both hydrogen, and $Z^1$ and $Z^2$ are both a single bond.

It is believed that the —C(=N—$Z^1$—$R^1$)—NH—$Z^2$—$R^2$ motif is particularly important for the stabilising effect of the stabilising agent (iii). In particular, it is believed that the —C(=N—$Z^1$—$R^1$)—NH—$Z^2$—$R^2$ motif mimics an arginine moiety of a substrate for the Factor VII polypeptide.

In more specific embodiments, the stabilising agent (iii) is at least one selected from the group consisting of amidine compounds comprising a —C—C(=N—$Z^1$—$R^1$)—NH—$Z^2$—$R^2$ motif and guanidines compounds comprising a >N—C(=N—$Z^1$—$R^1$)—NH—$Z^2$—$R^2$ motif.

In some embodiments, the stabilising agent (iii) is at least one amidine compound selected from the group consisting of benzamidines comprising the motif —$C_6H_4$—C(=N—$Z^1$—$R^1$)—NH—$Z^2$—$R^2$, wherein $C_6H_4$ denotes an optionally substituted benzene ring, of which benzamidine ($R^1$ and $R^2$ are hydrogen and $Z^1$ and $Z^2$ are a single bond) constitutes a particular embodiment (see the Experimental section).

In other particular embodiments thereof, the benzamidines comprises the motif >N—$C_6H_4$—C(=N—$Z^1$—$R^1$)—NH—$Z^2$—$R^2$, wherein $C_6H_4$ denotes an optionally substituted benzene ring, i.e. an o-amino-benzamidine, a m-amino-benzamidine or a p-amino-benzamidine, of which a p-amino-benzamidine is the currently most preferred.

Further illustrative examples of p-amino-benzamidines are those disclosed by Aventis in EP 1 162 194 A1, cf. in particular those defined in claims 1-6 and in sections [0009]-[0052], and in EP 1 270 551 A1, cf. in particular claims 1 and 2 and sections [0010]-[0032].

In another embodiment, the stabilising agent (iii) is at least one guanidine compound selected from the group consisting of guanidines compounds comprising a —$CH_2$—NH—C(=N—$Z^1$—$R^1$)—NH—$Z^2$—$R^2$ motif. Examples of guanidine compounds are those selected from the group consisting of arginine, arginine derivatives and peptides of 2-5 amino acid residues comprising at least one arginine residue. Arginine constitutes a particular embodiment (see the Experimental section).

The term "arginine derivatives" is intended to encompass arginine homologues, N-terminal functionalised arginines (e.g. N-methylated and N-acylated (e.g. acetylated) derivatives), C-terminal functionalised arginines (e.g. C-amidated, C-alkylamidated, and C-alkylated derivatives), and combinations thereof.

As mentioned above, the one crucial motif of the stabilising agents is —C(=N—$Z^1$—$R^1$)—NH—$Z^2$—$R^2$. Other parts of the stabilising agent may also be important, in particular with respect to optimisation of the stabilising effect and the tolerance by the patient. Typically, the stabilising agent has the formula Y—C(=N—$Z^1$—$R^1$)—NH—$Z^2$—$R^2$, wherein Y is an organic radical. The radical Y is typically selected in order to improve the efficiency of the stabilising effect. Also, the radical Y may comprise one or more further motifs of the formula —C(=N—$Z^1$—$R^1$)—NH—$Z^2$—$R^2$.

The molecular weight of the stabilising agent is typically at the most 1000 Da, such as at the most 500 Da.

The compounds of the present invention may have one or more asymmetric centres and unless otherwise indicated it is intended that stereoisomers (optical isomers), as separated, pure or partially purified stereoisomers or racemic mixtures thereof are included in the scope of the invention.

The concentration of the stabilising agent (or agents) (iii) is typically at least 1 μM. The desirable (or necessary) concentration typically depends on the selected stabilising agent (or agents), more specifically on the binding affinity of the selected stabilising agent to the Factor VII polypeptide.

In different embodiments, the stabilising agent (iii) is present in a concentration of at least 5 μM, at least 10 μM, at least 20 μM, at least 50 μM, at least 100 μM, at least 150 μM, at least 250 μM, at least 500 μM, at least 1 mM, at least 2 mM, at least 4 mM, at least 5 mM, at least 8 mM, at least 9 mM, at least 10 mM, at least 15 mM, at least 20 mM, such as, e.g., in the range of 1-10000 μM, 10-10000 μM, 20-10000 μM, 50-10000 μM, 10-5000 μM, 10-2000 μM, 20-5000 μM, 20-2000 μM, 50-5000 μM, 0.1-100 mM, 0.1-75 mM, 0.1-50 mM, 0.1-10 mM, 0.2-75 mM, 0.2-50 mM, 0.2-20 mM, 0.5-75 mM, or 0.5-50 mM.

In one embodiment, the stabilising agent (iii) is benzamidine and the concentration of said agent is at least 1 mM, such as, e.g., at least 2 mM, although it is envisaged that substituted benzamidines may be more potent for what reason they can be added in lower concentrations.

In one embodiment, the stabilizing agent (iii) is not benzamidine.

In one embodiment, the stabilising agent (iii) is arginine and the concentration of said agent is at least 10 mM, such as, e.g., at least 50 mM.

In another embodiment, the stabilising agent (iii) is p-amino-benzamidine and the concentration of said agent is at least 0.001 mM In another embodiment, the stabilising agent (iii) is 2-[3-(4-Carbamimidoylphenyl)-ureido]-N-[(S)-1-(3-methoxyphenyl)-ethyl]-acetamide with the formula.

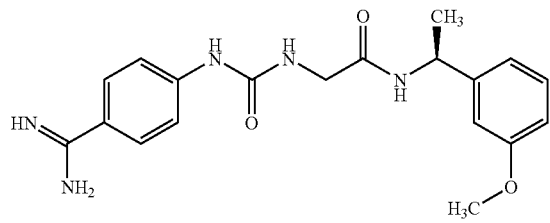

and the concentration of said agent is at least 0.001 mM.

In another embodiment, the stabilising agent (iii) is S-2-[3-(4-Carbamimidoylphenyl)-ureido]-N-(1-phenylethyl)-acetamide with the formula

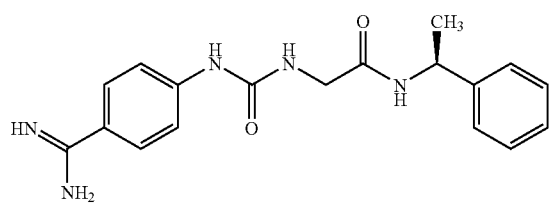

and the concentration of said agent is at least 0.001 mM.

In another embodiment, the stabilising agent (iii) is N-(3-Bromobenzyl)-2-[3-(4-carbamimidoylphenyl)-ureido]-acetamide with the formula

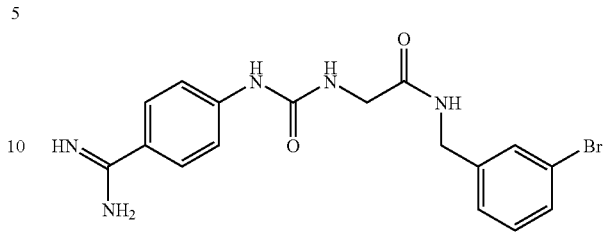

and the concentration of said agent is at least 0.001 mM.

In various embodiments, the molar ratio between the stabilising agent (iii) and FVII polypeptide (agent (iii):FVII) is: above 0.1, above 0.5, above 1, above 2, above 5, above 10, above 25, above 100, above 250, above 1000, above 2500, or above 5000, such as, e.g., in the range of 0.1-10000, 0.1-5000, 0.1-2500, 0.1-1000, 0.1-250, 0.1-100, 0.1-25, 0.1-10, 0.5-10000, 0.5-5000, 0.5-2500, 0.5-1000, 0.5-250, 0.5-100, 0.5-25, 0.5-10, 1-10000, 1-5000, 1-2500, 1-1000, 1-250, 1-100; 1-25; 1-10, 10-10000, 10-5000, 10-250, 1000-10000, or 1000-5000.

The desirable concentration typically depends on the selected stabilising agent (or agents), more specifically on the binding affinity of the selected agent to the Factor VII polypeptide.

The biological effect of the pharmaceutical composition is mainly ascribed to the presence of the Factor VII polypeptide, although other active ingredients may be included in combination with the Factor VII polypeptide.

As used herein, the term "Factor VII polypeptide" encompasses wild-type Factor VII (i.e. a polypeptide having the amino acid sequence disclosed in U.S. Pat. No. 4,784,950), as well as variants of Factor VII exhibiting substantially the same or improved biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VII polypeptide" also encompasses polypeptides, including variants, in which the Factor VIIa biological activity has been substantially modified or somewhat reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The biological activity of Factor VIIa in blood clotting derives from its ability to (i) bind to Tissue Factor (TF) and (ii) catalyze the proteolytic cleavage of Factor IX or Factor X to produce activated Factor IX or X (Factor IXa or Xa, respectively).

For the purposes of the invention, biological activity of Factor VII polypeptides ("Factor VII biological activity") may be quantified by measuring the ability of a preparation to promote blood clotting, cf. Assay 4 described herein. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) measuring the ability of Factor VIIa or a Factor VII-related polypeptide to produce activated Factor X (Factor Xa) in a system comprising TF embedded in a lipid membrane and Factor X. (Persson et al., J. Biol. Chem. 272:19919-19924, 1997); (ii) measuring Factor X hydrolysis in an aqueous system ("In Vitro Proteolysis Assay", see Assay 2 below); (iii) measuring the physical binding of Factor VIIa or a Factor VII-related polypeptide to TF using an instrument based on surface plasmon resonance (Persson, FEBS Letts. 413:359-363, 1997); (iv) measuring hydrolysis of a synthetic substrate by Factor VIIa and/or a Factor VII-related polypeptide ("In Vitro Hydrolysis Assay", see Assay 1 below); or (v) measuring generation of thrombin in a TF-independent in vitro system (see Assay 3 below).

Factor VII variants having substantially the same or improved biological activity relative to wild-type Factor VIIa encompass those that exhibit at least about 25%, such as, e.g., at least about 50%, at least about 75% or at least about 90% of the specific activity of Factor VIIa that has been produced in the same cell type, when tested in one or more of a clotting assay (Assay 4), proteolysis assay (Assay 2), or TF binding assay as described above. Factor VII variants having substantially reduced biological activity relative to wild-type Factor VIIa are those that exhibit less than about 25%, such as, e.g., less than about 10%, or less than about 5% of the specific activity of wild-type Factor VIIa that has been produced in the same cell type when tested in one or more of a clotting assay (Assay 4), proteolysis assay (Assay 2), or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of Factor VII variants having increased biological activity compared to wild-type FVIIa include FVII variants as disclosed in WO 01/83725, WO 02/22776, WO 02/077218, WO 03/27147, WO 03/37932; WO 02/38162 (Scripps Research Institute); and FVIIa variants with enhanced activity as disclosed in JP 2001061479 (Chemo-Sero-Therapeutic Res Inst.).

Non-limiting examples of Factor VII variants having substantially reduced or modified biological activity relative to wild-type Factor VII include R152E-FVIIa (Wildgoose et al., Biochem 29:3413-3420, 1990).

Examples of Factor VII polypeptides include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/

V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M 298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, E296V/K337A/V158T/S314E-FVII, M298Q/K337A/V158T/S314E-FVII, V158D/E296V/M298Q/K337A-FVII, V158D/E296V/M298Q/K337A/S314E-FVII, V158D/M298Q/K337A/S314E-FVII, E296V/M298Q/K337A/V158T/S314E-FVII, F374Y/L305V/V158D/E296V/M298Q/K337A/S314E-FVII,

S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys, and FVII having substitutions, deletions, or additions in the amino acid sequence Ile153-Arg223.

In some embodiments, the Factor VII polypeptide is human Factor VIIa (hFVIIa), preferably recombinantly made human Factor VIIa (rhVIIa).

In other embodiments, the Factor VII polypeptide is a Factor VII sequence variant.

In some embodiments, the Factor VII polypeptide has a glycosylation different from wild-type human Factor VII.

In various embodiments, e.g. those where the Factor VII polypeptide is a Factor VII-related polypeptide or a Factor VII sequence variant, the ratio between the activity of the Factor VII polypeptide and the activity of native human Factor VIIa (wild-type FVIIa) is at least about 1.25, preferably at least about 2.0, or 4.0, most preferred at least about 8.0, when tested in the "In Vitro Proteolysis Assay" (Assay 2) as described in the present specification.

In some embodiments, the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see Assay 1 below); in other embodiments, the ratio is at least about 2.0; in further embodiments, the ratio is at least about 4.0.

In a pharmaceutical composition, it is often desirable that the concentration of the active ingredient is such that the application of a unit dose does not cause unnecessary discomfort to the patient. Thus, a unit dose of more than about 2-10 mL is often undesirable. For the purpose of the present invention, the concentration of the Factor VII polypeptide is therefore at least 0.01 mg/mL. In different embodiments, the Factor VII polypeptide is present in a concentration of 0.01-20 mg/mL; 0.1-20 mg/mL; 0.1-15 mg/mL; 0.1-10 mg/mL; 0.5-5.0 mg/mL; 0.6-4.0 mg/mL; 1.0-4.0 mg/mL; 0.1-5 mg/mL; 0.1-4.0 mg/mL; 0.1-2 mg/mL; or 0.1-1.5 mg/mL.

Factor VIIa concentration is conveniently expressed as mg/mL or as IU/mL, with 1 mg usually representing 43,000-56,000 IU or more.

In order to render the liquid, aqueous pharmaceutical composition useful for direct parenteral administration to a mammal such as a human, it is normally required that the pH value of the composition is held within certain limits, such as from about 4.0 to about 9.0. To ensure a suitable pH value under the conditions given, the pharmaceutical composition also comprises a buffering agent (ii) suitable for keeping pH in the range of from about 4.0 to about 9.0.

The term "buffering agent" includes those agents or combinations of agents that maintain the solution pH in an acceptable range from about 4.0 to about 9.0.

In one embodiment, the buffering agent (ii) is at least one component selected from the groups consisting of acids and salts of MES, PIPES, ACES, BES, TES, HEPES, TRIS, histidine (e.g. L-histidine), imidazole, glycine, glycylglycine, glycinamide, phosphoric acid (e.g. sodium or potassium phosphate), acetic acid (e.g. ammonium, sodium or calcium acetate), lactic acid, glutaric acid, citric acid (e.g. sodium or potassium citrate), tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc.

The concentration of the buffering agent is chosen so as to maintain the preferred pH of the solution. In various embodiments, the concentration of the buffering agent is 1-100 mM; 1-50 mM; 1-25 mM; or 2-20 mM.

In one embodiment, the pH of the composition is kept from about 4.0 to about 9.0; from 5.0 to about 9.0; from about 5.0 to about 8.0; such as from about 5.0 to about 7.5; from about 5.0 and about 7.0; from about 5.0 to about 6.5; from about 5.0 to about 6.0; from about 5.5 to about 7.0; from about 5.5 to about 6.5; from about 6.0 to about 7.0; from about 6.0 to about 6.5; from about 6.3 to about 6.7, or from about 5.2 to about 5.7.

In addition to the three mandatory components, the liquid, aqueous pharmaceutical composition may comprise additional components beneficial for the preparation, formulation, stability, or administration of the composition.

Hence, the pharmaceutical composition may also include a non-ionic surfactant. Surfactants (also known as detergents) generally include those agents which protect the protein from air/solution interface induced stresses and solution/surface induced stresses (e.g. resulting in protein aggregation).

Typical types of non-ionic surfactants are polysorbates, poloxamers, polyoxyethylene alkyl ethers, polyethylene/polypropylene block co-polymers, polyethyleneglycol (PEG), polyxyethylene stearates, and polyoxyethylene castor oils.

Illustrative examples of non-ionic surfactants are Tween®, polysorbate 20, polysorbate 80, Brij-35 (polyoxyethylene dodecyl ether), poloxamer 188, poloxamer 407, PEG8000, Pluronic® polyols, polyoxy-23-lauryl ether, Myrj 49, and Cremophor A.

In one embodiment, the non-ionic surfactant is present in an amount of 0.005-2.0% by weight.

Also, the composition may further comprise a tonicity modifying agent (v).

As used herein, the term "tonicity modifying agent" includes agents which contribute to the osmolality of the solution. The tonicity modifying agent (v) includes at least one agent selected from the group consisting of neutral salts, amino acids, peptides of 2-5 amino acid residues, monosaccharides, disaccharides, polysaccharides, and sugar alcohols. In some embodiments, the composition comprises two or more of such agents in combination.

By "neutral salt" is meant a salt that is neither an acid nor a base when dissolved in an aqueous solution.

In one embodiment, at least one tonicity modifying agent (v) is a neutral salt selected from the groups consisting of sodium salts, potassium salts, calcium salts, and magnesium salts, such as sodium chloride, potassium chloride, calcium chloride, calcium acetate, calcium gluconate, calcium laevulate, magnesium chloride, magnesium acetate, magnesium gluconate, and magnesium laevulate.

In a further embodiment, the tonicity modifying agent (v) includes sodium chloride in combination with at least one selected from the groups consisting of calcium chloride, calcium acetate, magnesium chloride and magnesium acetate.

In a still further embodiment, the tonicity modifying agent (v) is at least one selected from the group consisting of sodium chloride, calcium chloride, sucrose, glucose, and mannitol.

In different embodiments, the tonicity modifying agent (v) is present in a concentration of at least 1 mM, at least 5 mM, at least 10 mM, at least 20 mM, at least 50 mM, at least 100 mM, at least 200 mM, at least 400 mM, at least 800 mM, at least 1000 mM, at least 1200 mM, at least 1500 mM, at least 1800 mM, at least 2000 mM, or at least 2200 mM.

In one series of embodiments, the tonicity modifying agent (v) is present in a concentration of 5-2200 mM, such as 25-2200 mM, 50-2200 mM, 100-2200 mM, 200-2200 mM, 400-2200 mM, 600-2200 mM, 800-2200 mM, 1000-2200 mM, 1200-2200 mM, 1400-2200 mM, 1600-2200 mM, 1800-2200 mM, or 2000-2200 mM; 5-1800 mM, 25-1800 mM, 50-1800 mM, 100-1800 mM, 200-1800 mM, 400-1800 mM, 600-1800 mM, 800-1800 mM, 1000-1800 mM, 1200-1800 mM, 1400-1800 mM, 1600-1800 mM; 5-1500 mM, 25-1400 mM, 50-1500 mM, 100-1500 mM, 200-1500 mM, 400-1500 mM, 600-1500 mM, 800-1500 mM, 1000-1500 mM, 1200-1500 mM; 5-1200 mM, 25-1200 mM, 50-1200 mM, 100-1200 mM, 200-1200 mM, 400-1200 mM, 600-1200 mM, or 800-1200 mM.

In one embodiment of the invention, at least one tonicity modifying agent (v) is an ionic strength modifying agent (v/a).

As used herein, the term "ionic strength modifying agent" includes agents which contribute to the ionic strength of the solution. The agents include, but are not limited to, neutral salts, amino acids, peptides of 2 to 5 amino acid residues. In some embodiments, the composition comprises two or more of such agents in combination.

Non-limiting examples of ionic strength modifying agents (v/a) are neutral salts such as sodium chloride, potassium chloride, calcium chloride and magnesium chloride. In one embodiment, the agent (v/a) is sodium chloride.

The term "ionic strength" is the ionic strength of the solution ($\mu$) which is defined by the equation: $\mu = \frac{1}{2}\Sigma[i](Z_i^2)$, where $\mu$ is the ionic strength, [i] is the millimolar concentration of an ion, and $Z_i$ is the charge (+ or −) of that ion "(see, e.g., Solomon, Journal of Chemical Education, 78(12):1691-92, 2001; James Fritz and George Schenk: Quantitative Analytical Chemistry, 1979).

In different embodiments of the invention, the ionic strength of the composition is at least 50 mM, such as at least 75 mM, at least 100 mM, at least 150 mM, at least 200 mM, at least 250 mM, at least 400 mM, at least 500 mM, at least 650 mM, at least 800 mM, at least 1000 mM, at least 1200 mM, at least 1600 mM, at least 2000 mM, at least 2400 mM, at least 2800 mM, or at least 3200 mM.

In some specific embodiments, the total concentration of the tonicity modifying agent (v) and the ionic strength modifying agent (v/a) is in the range of 1-1000 mM, such as 1-500 mM, 1-300 mM, 10-200 mM, or 20-150 mM; or such as 100-1000 mM, 200-800 mM, or 500-800 mM, depending on the effect any other ingredients may have on the tonicity and ionic strength.

In one embodiment, the composition is isotonic; in another, it is hypertonic.

The term "isotonic" means "isotonic with serum", i.e. at about 300±50 milliosmol/kg. The tonicity is meant to be a measure of osmolality of the solution prior to administration. The term "hypertonic" is meant to designate levels of osmolality above the physiological level of serum, such as levels above 300±50 milliosmol/kg.

Also, a particular embodiment of the present invention relates to the combination of the stabilising agent (iii) with a fairly high concentration of an ionic strength modifying agent (v/a). In one embodiment thereof, the ionic strength modifying agent (v/a) is selected from the group consisting of sodium salts, calcium salts and magnesium salts. In this embodiment, the ionic strength modifying agent (v/a), i.e. the sodium salt, calcium salt and/or magnesium salt, is present in a concentration of 15-1500 mM, such as 15-1000 mM, 25-1000 mM, 50-1000 mM, 100-1000 mM, 200-1000 mM, 300-1000 mM, 400-1000 mM, 500-1000 mM, 600-1000 mM, 700-1000 mM; 15-800 mM, 25-800 mM, 50-800 mM, 100-800 mM, 200-800 mM, 300-800 mM, 400-800 mM, 500-800 mM; 15-600 mM, 25-600 mM, 50-600 mM, 100-600 mM, 200-600 mM, 300-600 mM; 15-400 mM, 25-400 mM, 50-400 mM, or 100-400 mM.

Within these embodiments, sodium salt may be sodium chloride, the calcium salt may be selected from the group consisting of calcium chloride, calcium acetate, calcium gluconate, and calcium laevulate, and the magnesium salt may be selected from the group consisting of magnesium chloride, magnesium acetate, magnesium gluconate, magnesium laevulate, and magnesium salts of strong acids. In a more specific embodiment, a calcium salt and/or a magnesium salt is/are used in combination with sodium chloride.

In one embodiment, the composition comprises one or more ionic strength modifying agents selected from the group consisting of calcium ($Ca^{2+}$) salts and magnesium ($Mg^{2+}$) salts, e.g. one or more salts selected from the group consisting of calcium chloride, calcium acetate, calcium gluconate, calcium laevulate, magnesium chloride, magnesium acetate, magnesium sulphate, magnesium gluconate, magnesium laevulate, magnesium salts of strong acids.

In one embodiment, the Calcium (Ca2+) and/or Magnesium (Mg2+) is present in a concentration of at least about 0.1 μM, such as, e.g., at least about 0.5 μM, at least about 1 μM, at least about 5 μM, at least about 10 μM, at least about 50 μM, at least about 100 μM, at least about 1 mM, at least about 2 mM, at least about 5 mM, or at least about 10 mM. In a particular embodiment the composition comprises at least 2 mM Ca2+.

In various embodiments, the molar ratio between calcium (Ca2+) and/or magnesium ions (Mg2+) and FVII polypeptide is: 0.001-750; 0.001-250; 0.001-100; 0.001-10; 0.001-1.0; 0.001-0.5; 0.5-750; 0.5-250; 0.5-100; 0.5-10; 0.5-1.0; 0.001-0.4999; 0.005-0.050.

In one embodiment of the present invention, the molar ratio of non-complexed calcium (Ca2+) and/or magnesium (Mg2+) to the Factor VII polypeptide is lower than 0.5, e.g. in the range of 0.001-0.499, such as 0.005-0.050, or in the range of 0.000-0.499, such as in the range of 0.000-0.050, or about 0.000. In one embodiment of the present invention, the molar ratio of non-complexed calcium (Ca2+) to the Factor VII polypeptide is lower than 0.5, e.g. in the range of 0.001-0.499, such as 0.005-0.050, or in the range of 0.000-0.499, such as in the range of 0.000-0.050, or about 0.000.

When used herein, the term "the concentration of non-complexed calcium and/or magnesium ions" is intended to mean the difference between the total concentration of calcium and/or magnesium ions and the concentration of calcium and/or magnesium bound to calcium/magnesium chelators. In this regard, the Factor VII polypeptide is not regarded as a "calcium/magnesium chelator" although calcium and/or magnesium is expected to bind to, or become associated with, the Factor VII polypeptide under certain conditions.

In another embodiment, the molar ratio of non-complexed calcium and/or magnesium ions to the Factor VII polypeptide is above 0.5. In another embodiment, the molar ratio of non-complexed calcium ions to the Factor VII polypeptide is above 0.5.

In order to obtain the low relative ratio between calcium and/or magnesium ions (Ca2+) and the Factor VII polypeptide, it may be necessary or desirable to remove excess calcium and/or magnesium ions, e.g., by contacting the composition with an ion-exchange material under conditions suitable for removing Ca2+ and/or Mg2+, or to add a calcium/magnesium chelator in order to bind (complex) excess calcium and/or magnesium ions. This is particularly relevant where the ratio between calcium and/or magnesium ions and the Factor VII polypeptide in a solution from a process step preceding the formulation step exceeds the limit stated above. Examples of "calcium/magnesium chelators" include EDTA, citric acid, NTA, DTPA, tartaric acid, lactic acid, malic acid, succinic acid, HIMDA, ADA and similar compounds.

In a further embodiment, the composition further comprises an antioxidant (vi). In different embodiments, the antioxidant is selected from the group consisting of L-methionine, D-methionine, methionine analogues, methionine-containing peptides, methionine-homologues, ascorbic acid, cysteine, homocysteine, gluthatione, cystine, and cysstathionine. In a preferred embodiment, the antioxidant is L-methionine.

The concentration of the antioxidant is typically 0.1-5.0 mg/mL, such as 0.1-4.0 mg/mL, 0.1-3.0 mg/mL, 0.1-2.0 mg/ml, or 0.5-2.0 mg/mL.

In particular embodiments, the composition does not include an antioxidant; instead the susceptibility of the Factor VII polypeptide to oxidation is controlled by exclusion of atmospheric air. The use of an antioxidant may of course also be combined with the exclusion of atmospheric air.

Thus, the present invention also provides an air-tight container (e.g. a vial or a cartridge (such as a cartridge for a pen applicator)) containing a liquid, aqueous pharmaceutical composition as defined herein, and optionally an inert gas.

The inert gas may be selected from the groups consisting of nitrogen, argon, etc. The container (e.g. vial or cartridge) is typically made of glass or plastic, in particular glass, optionally closed by a rubber septum or other closure means allowing for penetration with preservation of the integrity of the pharmaceutical composition. In a particular embodiment hereof, the composition does not comprise a preservative (vii). In a further embodiment, the container is a vial or cartridge enclosed in a sealed bag, e.g. a sealed plastic bag, such as a laminated (e.g. metal (such as aluminium) laminated plastic bag).

In addition to the mandatory components, the non-ionic surfactant (iv), the tonicity modifying agent (v) and the optional antioxidant (vi), the pharmaceutical composition may further comprise a preservative (vii).

A preservative may be included in the composition to retard microbial growth and thereby allow "multiple use" packaging of the Factor VII polypeptides. Examples of preservatives include phenol, benzyl alcohol, orto-cresol, meta-cresol, para-cresol, methyl paraben, propyl paraben, benzalkonium chloride, and benzethonium chloride. The preservative is normally included at a concentration of 0.1-20 mg/mL depending on the pH range and type of preservative.

Still further, the composition may also include one or more agents capable of inhibiting deamidation and isomerisation.

In one embodiment, the liquid, aqueous pharmaceutical composition comprises:

0.1-20 mg/mL of a Factor VII polypeptide (i);

a buffering agent (ii) suitable for keeping pH in the range of from about 4.0 to about 9.0;

at least one stabilising agent (iii) comprising the motif $-C_6H_4-C(=N-Z^1-R^1)-NH-Z^2-R^2$ in a concentration of at least 5 µM;

a non-ionic surfactant (iv); and at least one tonicity modifying agent (v) in a concentration of at least 5 mM.

In another embodiment, the liquid, aqueous pharmaceutical composition comprises:

0.1-10 mg/mL of a Factor VII polypeptide (i);

a buffering agent (ii) suitable for keeping pH in the range of from about 4.0 to about 9.0;

at least one stabilising agent (iii) comprising the motif $-CH_2-NH-C(=N-Z^1-R^1)-NH-Z^2-R^2$ in a concentration of at least 500 µM;

a non-ionic surfactant (iv); and at least one tonicity modifying agent (v) in a concentration of at least 5 mM.

As used herein, pH values specified as "about" are understood to be ±0.1, e.g. about pH 8.0 includes pH 8.0±0.1.

Percentages are (weight/weight) both when referring to solids dissolved in solution and liquids mixed into solutions. For example, for Tween®, it is the weight of 100% stock/weight of solution.

The compositions according to the present invention are useful as stable and preferably ready-to-use compositions of Factor VII polypeptides. Furthermore, it is believed that the principles, guidelines and specific embodiments given herein are equally applicable for bulk storage of Factor VII polypeptides, mutatis mutandis. The compositions are typically stable for at least six months, and preferably up to 36 months; when stored at temperatures ranging from 2° C. to 8° C. The compositions are chemically and/or physically stable, in particular chemically stable, when stored for at least 6 months at from 2° C. to 8° C.

The term "Stable" is intended to denote that (i) after storage for 6 months at 2° C. to 8° C. the composition retains at least 50% of its initial biological activity as measured by a one-stage clot assay essentially as described in Assay 4 of the present specification, or (ii) after storage for 6 months at 2° C. to 8° C., the increase in content of heavy chain degradation products is at the most 40% (w/w) of the initial content of Factor VII polypeptide.

The term "initial content" relates to the amount of Factor VII polypeptides added to a composition upon preparation of the composition.

In one embodiment, the stable composition retains at least 70%, such as, e.g., at least 80%, at least 85%, at least 90%, or at least 95%, of its initial biological activity after storage for 6 months at 2 to 8° C.

In different embodiments of the invention, the stable composition further retains at least 50% of its initial biological activity as measured by a one-stage clot assay essentially as described in Assay 4 of the present specification after storage for at least 30 days, such as 60 days or 90 days.

In various embodiments the increase in content of heavy chain degradation products in the stable compositions is not more than about 30% (w/w), not more than about 25% (w/w), not more than about 20% (w/w), not more than about 15% (w/w), not more than about 10% (w/w), not more than about 5% (w/w), or not more than about 3% (w/w) of the initial content of Factor VII polypeptide.

For the purpose of determining the content of heavy chain degradation products, a reverse phase HPLC was run on a proprietary 4.5×250 mm butyl-bonded silica column with a particle size of 5 µm and pore size 300 Å. Column temperature: 70° C. A-buffer: 0.1% v/v trifluoracetic acid. B-buffer: 0.09% v/v trifluoracetic acid, 80% v/v acetonitrile. The column was eluted with a linear gradient from X to (X+13) % B in 30 minutes. X was adjusted so that FVIIa elutes with a retention time of approximately 26 minutes. Flow rate: 1.0 mL/min. Detection: 214 nm. Load: 25 µg FVIIa.

The term "physical stability" of Factor VII polypeptides relates to the formation of insoluble and/or soluble aggregates in the form of dimeric, oligomeric and polymeric forms of Factor VII polypeptides as well as any structural deformation and denaturation of the molecule. Physically stable composition encompasses compositions which remains visually clear. Physical stability of the compositions is often evaluated by means of visual inspection and turbidity after storage of the composition at different temperatures for various time periods. Visual inspection of the compositions is performed in a sharp focused light with a dark background. A composition is classified as physically unstable, when it shows visual turbidity.

The term "chemical stability" is intended to relate to the formation of any chemical change in the Factor VII polypeptides upon storage in solution at accelerated conditions. Examples are hydrolysis, deamidation and oxidation as well as enzymatic degradation resulting in formation of fragments of Factor VII polypeptides. In particular, the sulphur-containing amino acids are prone to oxidation with the formation of the corresponding sulphoxides.

The term "chemically stable" is intended to designate a composition which retains at least 50% of its initial biological activity after storage for 6 months at 2 to 8° C., as measured by a one-stage clot assay (Assay 4).

In a further aspect, the invention also provides a method for preparing a liquid, aqueous pharmaceutical composition of a Factor VII polypeptide, comprising the step of providing the Factor VII polypeptide at a concentration of at least 0.01 mg/mL (i) in a solution comprising a buffering agent (ii) suitable for keeping pH in the range of from about 4.0 to about 9.0; and at least one stabilising agent (iii) comprising a $-C(=N-Z^1-R^1)-NH-Z^2-R^2$ motif, wherein $Z^1$ and $Z^2$ independently are selected from the group consisting of $-O-$, $-S-$, $-NR^H-$ and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, or $Z^2$ and $R^2$ are as defined above and $-C=N-Z^1-R^1$ forms part of a heterocyclic ring, or $Z^1$ and $R^1$ are as defined above and $-C-NH-Z^2-R^2$ forms part of a heterocyclic ring, or $-C(=N-Z^1-R^1)-NH-Z^2-R^2$ forms a heterocyclic ring wherein $-Z^1-R^1-R^2-Z^2-$ is a biradical.

Methods of Use

As will be understood, the liquid, aqueous pharmaceutical compositions defined herein can be used in the field of medicine. Thus, the present invention in particular provides the liquid, aqueous pharmaceutical compositions defined herein for use as a medicament, more particular for use as a medicament for treating a Factor VII-responsive syndrome.

Consequently, the present invention also provides the use of the liquid, aqueous pharmaceutical composition as defined herein for the preparation of a medicament for treating a Factor VII-responsive syndrome, as well as a method for treating a Factor VII-responsive syndrome, the method comprising administering to a subject in need thereof an effective amount of the liquid, aqueous pharmaceutical composition as defined herein.

The preparations of the present invention may be used to treat any Factor VII-responsive syndrome, such as, e.g., bleeding disorders, including those caused by clotting Factor deficiencies (e.g., e.g. haemophilia A, haemophilia B, coagulation Factor XI deficiency, coagulation Factor VII deficiency); by thrombocytopenia or von Willebrand's disease, or by clotting Factor inhibitors, and intra cerebral hemorrhage, or excessive bleeding from any cause. The preparations may also be administered to patients in association with surgery or other trauma or to patients receiving anticoagulant therapy.

The term "effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment, patient-related factors (e.g. weight, health, age, etc.), presence of co-administered medications (e.g., anticoagulants), time of administration, or other factors known to a medical practitioner.

The term "treatment" is defined as the management and care of a subject, e.g. a mammal, in particular a human, for the purpose of combating the disease, condition, or disorder and includes the administration of a Factor VII polypeptide to prevent the onset of the symptoms or complications, or alleviating the symptoms or complications, or eliminating the disease, condition, or disorder. Pharmaceutical compositions according to the present invention containing a Factor VII polypeptide may be administered parenterally to subjects in need of such a treatment. Parenteral administration may be performed by subcutaneous, intramuscular or intravenous injection by means of a syringe, optionally a pen-like syringe. Alternatively, parenteral administration can be performed by means of an infusion pump.

In important embodiments, the pharmaceutical composition is adapted to subcutaneous, intramuscular or intravenous injection according to methods known in the art.

EXPERIMENTALS

General Methods

Assays Suitable for Determining Biological Activity of Factor VII Polypeptides

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

In Vitro Hydrolysis Assay (Assay 1)

Native (wild-type) Factor VIIa and Factor VII polypeptide (both hereinafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM HEPES, pH 7.4, containing 0.1 M NaCl, 5 mM $CaCl_2$ and 1 mg/mL bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used for calculating the ratio between the activities of Factor VII polypeptide and wild-type Factor VIIa:

Ratio=($A$405 nm Factor *VII* polypeptide)/($A$405 nm Factor *VIIa* wild-type).

Based thereon, Factor VII polypeptides with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

The activity of the Factor VII polypeptides may also be measured using a physiological substrate such as Factor X ("In Vitro Proteolysis Assay"), suitably at a concentration of 100-1000 nM, where the Factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereinafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 μL 50 mM HEPES, pH 7.4, containing 0.1 M NaCl, 5 mM $CaCl_2$ and 1 mg/mL bovine serum albumin, are incubated for 15 min. Factor X cleavage is then stopped by the addition of 50 μL 50 mM HEPES, pH 7.4, containing 0.1 M NaCl, 20 mM EDTA and 1 mg/mL bovine serum albumin. The amount of Factor Xa generated is measured by the addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used for calculating the ratio between the proteolytic activities of Factor VII polypeptide and wild-type Factor VIIa:

Ratio=($A$405 nm Factor *VII* polypeptide)/($A$405 nm Factor *VIIa* wild-type).

Based thereon, Factor VII polypeptide with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

Thrombin Generation Assay (Assay 3)

The ability of Factor VIIa or Factor VII polypeptides to generate thrombin can also be measured in an assay (Assay 3) comprising all relevant coagulation Factors and inhibitors at physiological concentrations (minus Factor VIII when mimicking hemophilia A conditions) and activated platelets (as described on p. 543 in Monroe et al. (1997) Brit. J. Haematol. 99, 542-547, which is hereby incorporated herein as reference).

One-stage Coagulation Assay (Clot Assay) (Assay 4)

Factor VII polypeptides may also be assayed for specific activities ("clot activity") by using a one-stage coagulation assay (Assay 4). For this purpose, the sample to be tested is diluted in 50 mM PIPES-buffer (pH 7.5), 0.1% BSA and 40 μl is incubated with 40 μl of Factor VII deficient plasma and 80 μl of human recombinant tissue factor containing 10 mM Ca2+ and synthetic phospholipids. Coagulation times (clotting times) are measured and compared to a standard curve using a reference standard in a parallel line assay.

Preparation and Purification of Factor VII Polypeptides

Human purified Factor VIIa suitable for use in the present invention is preferably made by DNA recombinant technology, e.g. as described by Hagen et al., Proc. Natl. Acad. Sci. USA 83: 2412-2416, 1986, or as described in European Patent No. 0 200 421 (ZymoGenetics, Inc.).

Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield Factor VII without detectable amounts of other blood coagulation Factors. An even further purified Factor VII preparation may be obtained by including an additional gel filtration as the final purification step. Factor VII is then converted into activated Factor VIIa by known means, e.g. by several different plasma proteins, such as Factor XIIa, IX a or Xa. Alternatively, as described by Bjoern et al. (Research Disclosure, 269 September 1986, pp. 564-565), Factor VII may be activated by passing it through an ion-exchange chromatography column, such as Mono Q® (Pharmacia fine Chemicals) or the like, or by autoactivation in solution.

Factor VII-related polypeptides may be produced by modification of wild-type Factor VII or by recombinant technology. Factor VII-related polypeptides with altered amino acid sequence when compared to wild-type Factor VII may be produced by modifying the nucleic acid sequence encoding wild-type Factor VII either by altering the amino acid codons or by removal of some of the amino acid codons in the nucleic acid encoding the natural Factor VII by known means, e.g. by site-specific mutagenesis.

It will be apparent to those skilled in the art that substitutions can be made outside the regions critical to the function of the Factor VIIa molecule and still result in an active polypeptide. Amino acid residues essential to the activity of the Factor VII polypeptide, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super-coiled, double-stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemi-methylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than 10% by weight, more preferably less than 5% and most preferably less than 1%, of non-Factor VII polypeptides derived from the host cell.

Factor VII polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII polypeptides may be activated by passing it through an ion-exchange chromatography column, such as Mono Q® (Pharmacia) or the like, or by autoactivation in solution. The resulting activated Factor VII polypeptide may then be formulated and administered as described in the present application.

The following examples illustrate practice of the invention. These examples are included for illustrative purposes only and are not intended in any way to limit the scope of the invention claimed.

WORKING EXAMPLES

In the below working examples the content of heavy chain degradation products is determined by RP-HPLC as described in the following:

Reverse phase HPLC was run on a proprietary 4.5×250 mm butyl-bonded silica column with a particle size of 5 μm and pore size 300 Å. Column temperature: 70° C. A-buffer: 0.1% v/v trifluoracetic acid. B-buffer: 0.09% v/v trifluoracetic acid, 80% v/v acetonitrile. The column was eluted with a linear gradient from X to (X+13) % B in 30 minutes. X was adjusted so that FVIIa elutes with a retention time of approximately 26 minutes. Flow rate: 1.0 mL/min. Detection: 214 nm. Load: 25 μg FVIIa.

In the below examples the clot activity is measured using a one stage clot assay essentially as described in Assay 4 of the present specification.

Example 1

In order to investigate the effect of benzamidine on the stability of rFVIIa the following formulations were prepared:
Formulation 1:
1.0 mg/mL rFVIIa
10 mM Histidine
10 mM Sodium acetate 10 mM Glycylglycine
50 mM Sodium chloride
10 mM Calcium chloride
50 mM Benzamidine
pH=6.5

Formulation 2:
1.0 mg/mL rFVIIa
10 mM Histidine
10 mM Sodium acetate
10 mM Glycylglycine
50 mM Sodium chloride
10 mM Calcium chloride
50 mM Benzamidine
pH=7.0

Formulation 3:
1.0 mg/mL rFVIIa
10 mM Histidine
10 mM Sodium acetate
10 mM Glycylglycine
50 mM Sodium chloride Formulation 4:
1.0 mg/mL rFVIIa
10 mM Histidine
10 mM Sodium acetate
10 mM Glycylglycine
50 mM Sodium chloride
10 mM Calcium chloride
pH=7.0

The formulations were prepared by adding 10 mM histidine, 10 mM sodium acetate and 50 mM benzamidine (only for formulations 1 and 2) to a 1.0 mg/mL bulk solution of rFVIIa already containing glycylglycine, sodium chloride and calcium chloride in the above mentioned concentrations. pH was finally adjusted to 6.5 and 7.0, respectively, with 1 M sodium hydroxide and 1 M hydrochloric acid.

The formulations were stored at a temperature of 5° C. and 30° C., and the analyses for formation of Heavy chain degradation products were performed at time points shown in the table (Table 1).

v/v trifluoroacetic acid. B-buffer: 0.09% v/v trifluoroacetic acid, 80% v/v acetonitrile. The column was eluted with a linear gradient from X to (X+13)% B in 30 minutes. X was adjusted so that FVIIa elutes with a retention time of approximately 26 minutes. Flow rate: 1.0 mL/min. Detection: 214 nm. Load: 25 µg FVIIa.

Example 2

In order to investigate the effect of arginine on the stability of rFVIIa the following solutions were prepared:

Formulation 5:
1.0 mg/mL rFVIIa
25 mM HEPES
10 mM Glycylglycine
50 mM Sodium chloride
10 mM Calcium chloride
pH=7.5

Formulation 6:
1.0 mg/mL rFVIIa
25 mM HEPES
10 mM Glycylglycine
50 mM Sodium chloride
10 mM Calcium chloride
200 mM Arginine
pH=7.5

Formulation 7:
1.0 mg/mL rFVIIa
20 mM Histidine
20 mM Glycylglycine
50 mM Sodium chloride
10 mM Calcium chloride
pH=7.0

Formulation 8:
1.0 mg/mL rFVIIa
50 mM Histidine
50 mM Glycylglycine
50 mM Sodium chloride
10 mM Calcium chloride
200 mM Arginine
pH=7.0

TABLE 1

Formation of Heavy chain degradation (hcd) products in benzamidine formulations

| Formulation | % hcd 0 months | % hcd ½ months 30° C. | % hcd 1 months 30° C. | % hcd 1 months 5° C. | % hcd 2 months 30° C. | % hcd 2 months 5° C. | % hcd 3 months 30° C. | % hcd 3 months 5° C. | % hcd 6 months 30° C. | % hcd 6 months 5° C. | % hcd 14 months 5° C. |
|---|---|---|---|---|---|---|---|---|---|---|---|
| 1 (pH 6.5) | 7.5 | 9.5 | 11.6 | 7.5 | 14.6 | 7.7 | 17.5 | 8.1 | 20.4 | 8.9 | 10.5 |
| 2 (pH 7.0) | 7.3 | 12.4 | 17.2 | 8.0 | 23.5 | 8.6 | 28.4 | 9.4 | 31.5 | 11.5 | 15.4 |
| 3 (pH 6.5) | 8.1 | — | 17.7 | 16.3 | 22.7 | — | — | 30.2 | 25.7 | 42.1 | — |
| 4 (pH 7.0) | 9.6 | — | 29.9 | 32.5 | 38.6 | — | — | 56.9 | 45.5 | 67.3 | — |

As it can be seen from Table 1, after 6 months of storage at 5° C. the increase in the content of Heavy chain degradation products in the reference formulations (3 and 4) was 34.0% and 57.7%, respectively, whereas the increase in the content of Heavy chain degradation products in the illustrative compositions (1 and 2) was only 1.4% and 4.2%, respectively. After 14 months of storage at 5° C., the increase in the content of Heavy chain degradation products in the illustrative compositions (1 and 2) was only 3.0% and 8.1%, respectively.

The content of heavy chain degradation products is determined by RP-HPLC as described in the following:

Reverse phase HPLC was run on a proprietary 4.5×250 mm butyl-bonded silica column with a particle size of 5 µm and pore size 300 Å. Column temperature: 70° C. A-buffer: 0.1%

Formulation 9
1.0 mg/mL rFVIIa
50 mM Histidine
50 mM Glycylglycine
50 mM Sodium chloride
10 mM Calcium chloride
400 mM Arginine
pH=7.0

The formulations were prepared by adding 25 mM HEPES (solutions 5 and 6) and arginine (solutions 6, 8 and 9) to a 1.0 mg/mL bulk solution of rFVIIa already containing glycylglycine, sodium chloride and calcium chloride in the above mentioned concentrations. pH was finally adjusted with 1 M sodium hydroxide and 1 M hydrochloric acid.

The formulations were stored at a temperature of 5° C. and 30° C., and the analyses for formation of heavy chain degradation products were performed as in Example 1 at time points shown in the Table 2.

TABLE 2

Formation of heavy chain degradation products (hcd) in arginine formulations

| Formulation | % hcd 0 months | % hcd ½ months 30° C. | % hcd ½ months 5° C. | % hcd 1 months 30° C. | % hcd 1 months 5° C. | % hcd 2 months 30° C. | % hcd 2 months 5° C. | % hcd 3 months 30° C. | % hcd 3 months 5° C. |
|---|---|---|---|---|---|---|---|---|---|
| 5 | 17.3 | 28.7 | 32.0 | 35.5 | 42.7 | 42.1 | 57.0 | 44.4 | 64.3 |
| 6 | 13.6 | 19.5 | 21.2 | 25.5 | 29.8 | 30.9 | 41.9 | 34.0 | 49.0 |
| 7 | 9.4 | — | n.a. | — | 31.7 | — | 44.6 | — | 52.5 |
| 8 | 11.7* | — | 17.3 | — | 23.0 | — | 31.1 | — | 37.7 |
| 9 | 11.5* | — | 14.0 | — | 17.4 | — | 21.5 | — | 25.4 |

*analysed at t = 3 days, a slight increase is expected from day 0 to day 3
n.a.: not analysed Example 3

Formulation of the following liquid, aqueous pharmaceutical compositions is envisaged:

A)

| | |
|---|---|
| rhFVIIa | 1 mg/mL (approx. 50,000 IU/mL) |
| PIPES | 15.12 mg/mL (50 mM) |
| Benzamidine | 50 mM |
| Poloxamer 188 | 0.5 mg/mL |
| Sodium chloride | 2.92 mg/mL (50 mM) |
| Calcium chloride 2 H$_2$O | 1.47 mg/mL (10 mM) |
| Methionine | 0.5 mg/mL |
| 1 M NaOH/1 M HCl | added to pH 6.5 |

B)

| | |
|---|---|
| rhFVIIa | 1 mg/mL (approx. 50,000 IU/mL) |
| PIPES | 15.12 mg/mL (50 mM) |
| p-Aminobenzamidine | 10 mM |
| Poloxamer 188 | 0.5 mg/mL |
| Sodium chloride | 2.92 mg/mL (50 mM) |
| Calcium chloride 2 H$_2$O | 1.47 mg/mL (10 mM) |
| Methionine | 0.5 mg/mL |
| 1 M NaOH/1 M HCl | added to pH 6.5 |

C)

| | |
|---|---|
| rhFVIIa | 1 mg/mL (approx. 50,000 IU/mL) |
| PIPES | 15.12 mg/mL (50 mM) |
| Arginine | 50 mM |
| Poloxamer 188 | 0.5 mg/mL |
| Sodium chloride | 2.92 mg/mL (50 mM) |
| Calcium chloride 2 H$_2$O | 1.47 mg/mL (10 mM) |
| 1 M NaOH/1 M HCl | added to pH 6.5 |

D)

| | |
|---|---|
| rhFVIIa | 1 mg/mL (approx. 50,000 IU/mL) |
| PIPES | 15.12 mg/mL (50 mM) |
| Arginine | 100 mM |
| Poloxamer 188 | 0.5 mg/mL |
| Sodium chloride | 2.92 mg/mL (50 mM) |
| Calcium chloride 2 H$_2$O | 1.47 mg/mL (10 mM) |
| 1 M NaOH/1 M HCl | added to pH 6.5 |

Pharmaceutical compositions A-D can subsequently be transferred to sterile vials or cartridges flushed with nitrogen or argon and can then be packed in air-tight aluminium-laminated plastic bags.

Example 4

In order to investigate the effect of benzamidine on the stability of rFVIIa the following formulations were prepared:

Formulation 1
1.0 mg/mL rFVIIa
10 mM Histidine
10 mM Glycylglycine
50 mM Sodium chloride
10 mM Calcium chloride
pH=6.5

Formulation 2
1.0 mg/mL rFVIIa
10 mM Histidine
10 mM Glycylglycine
50 mM Sodium chloride
10 mM Calcium chloride
50 mM Benzamidine
pH=6.5

Formulation 3
1.0 mg/mL rFVIIa
10 mM Histidine
10 mM Glycylglycine
50 mM Sodium chloride
10 mM Calcium chloride
pH=7.5

Formulation 4
1.0 mg/mL rFVIIa
10 mM Histidine
10 mM Glycylglycine
50 mM Sodium chloride
10 mM Calcium chloride
50 mM Benzamidine
pH=7.5

The formulations were prepared by adding 10 mM histidine and 50 mM benzamidine (only for formulations 2 and 4) to a 1.0 mg/mL bulk solution of rFVIIa already containing glycylglycine, sodium chloride and calcium chloride in the above-mentioned concentrations. pH was finally adjusted to 6.5 and 7.5, respectively, with 1 M sodium hydroxide and 1 M hydrochloric acid.

The formulations were stored at a temperature of 5° C. and the analyses for clot activity were performed at time points shown in Table 3:

TABLE 3

Clot activity (IU/mL)

Storage time at 5° C.(months)

| Formulation | 0 | 3 | 7 | 10 |
|---|---|---|---|---|
| 1 | 46.200 | 31.000 | <1.000 | Not analysed |
| 2 | 43.300 | 43.800 | 44.400 | 43.200 |
| 3 | 42.800 | 14.900 | 9.700 | Not analysed |
| 4 | 44.700 | 40.000 | 40.600 | 39.300 |

Example 5

In order to investigate the effect of different stabilizers on the stability of rFVIIa the following formulations were prepared:

Formulation 1
 1.0 mg/mL rFVIIa
 10 mM Histidine
 10 mM Glycylglycine
 50 mM Sodium chloride
 10 mM Calcium chloride
 pH=6.5

Formulation 2
 1.0 mg/mL rFVIIa
 10 mM Histidine
 10 mM Glycylglycine
 50 mM Sodium chloride
 10 mM Calcium chloride
 5 mM p-amino-Benzamidine
 pH=6.5

Formulation 3
 1.0 mg/mL rFVIIa
 10 mM Histidine
 10 mM Glycylglycine
 50 mM Sodium chloride
 10 mM Calcium chloride
 0.5 mM S-2-[3-(4-Carbamimidoylphenyl)-ureido]-N-[1-(3-methoxyphenyl)-ethyl]-acetamide
 pH=6.5

Formulation 4
 1.0 mg/mL rFVIIa
 10 mM Histidine
 10 mM Glycylglycine
 50 mM Sodium chloride
 10 mM Calcium chloride
 pH=7.5

Formulation 5
 1.0 mg/mL rFVIIa
 10 mM Histidine
 10 mM Glycylglycine
 50 mM Sodium chloride
 10 mM Calcium chloride
 5 mM p-amino-Benzamidine
 pH=7.5

Formulation 6
 1.0 mg/mL rFVIIa
 10 mM Histidine
 10 mM Glycylglycine
 50 mM Sodium chloride
 10 mM Calcium chloride
 0.5 mM S-2-[3-(4-Carbamimidoylphenyl)-ureido]-N-[1-(3-methoxyphenyl)-ethyl]-acetamide
 pH=7.5

The formulations were prepared by adding 10 mM histidine, 5 mM p-amino-Benzamidine (for formulations 2 and 5) and 0.5 mM S-2-[3-(4-Carbamimidoylphenyl)-ureido]-N-[1-(3-methoxyphenyl)-ethyl]-acetamide (for formulations 3 and 6) to a 1.0 mg/mL bulk solution of rFVIIa already containing glycylglycine, sodium chloride and calcium chloride in the above-mentioned concentrations. pH was finally adjusted to 6.5 and 7.5, respectively, with 1 M sodium hydroxide and 1 M hydrochloric acid.

The formulations were stored at a temperature of 5° C. and the analyses for clot activity (Table 4) and Heavy chain degradation (Table 5) were performed at the time points shown in the tables:

TABLE 4

Clot activity (IU/mL)

Storage time at 5° C.(months)

| Formulation | 0 | 3 | 6 | 9 |
|---|---|---|---|---|
| 1 | 42.400 | 29.300 | 23.500 | 20.600 |
| 2 | 40.700 | 46.700 | 39.500 | 41.200 |
| 3 | 43.400 | 42.400 | 39.700 | 44.200 |
| 4 | 38.900 | 16.200 | 9.800 | Not analysed |
| 5 | 44.900 | 42.500 | 37.800 | 35.900 |
| 6 | 39.800 | 41.200 | 45.700 | 43.100 |

TABLE 5

Content of Heavy chain degradation (%)

Storage time at 5° C.(months)

| Formulation | 0 | 1 | 3 | 6 |
|---|---|---|---|---|
| 1 | 12.9 | 23.6 | 38.0 | 51.1 |
| 2 | 12.1 | 12.5 | 13.4 | 15.2 |
| 3 | 12.1 | 11.5 | 10.9 | 12.0 |
| 4 | 16.9 | 54.0 | 71.5 | 76.7 |
| 5 | 12.7 | 16.7 | 22.0 | 29.1 |
| 6 | 11.9 | 11.3 | 11.3 | 11.7 |

Example 6

In order to investigate the effect of benzamidine and N-(3-Bromobenzyl)-2-[3-(4-carbamimidoylphenyl)-ureido]-acetamide, HCl on the stability of rFVIIa the following formulations were prepared:

Formulation 1
 1.0 mg/mL rFVIIa
 10 mM Histidine
 10 mM Glycylglycine
 50 mM Sodium chloride
 10 mM Calcium chloride
 pH=6.5

Formulation 2
 1.0 mg/mL rFVIIa
 10 mM Histidine
 10 mM Glycylglycine
 50 mM Sodium chloride
 10 mM Calcium chloride
 50 mM Benzamidine
 pH=6.5

Formulation 3
    1.0 mg/mL rFVIIa
    10 mM Histidine
    10 mM Glycylglycine
    50 mM Sodium chloride
    10 mM Calcium chloride
    50 µM N-(3-Bromobenzyl)-2-[3-(4-carbamimidoylphenyl)-ureido]-acetamide HCl
    pH=6.5
Formulation 4
    1.0 mg/mL rFVIIa
    10 mM Histidine
    10 mM Glycylglycine
    50 mM Sodium chloride
    10 mM Calcium chloride
    500 µM N-(3-Bromobenzyl)-2-[3-(4-carbamimidoylphenyl)-ureido]-acetamide HCl
    pH=6.5
Formulation 5
    1.0 mg/mL rFVIIa
    10 mM Histidine
    10 mM Glycylglycine
    50 mM Sodium chloride
    10 mM Calcium chloride
    pH=7.5
Formulation 6
    1.0 mg/mL rFVIIa
    10 mM Histidine
    10 mM Glycylglycine
    50 mM Sodium chloride
    10 mM Calcium chloride
    50 mM Benzamidine
    pH=7.5
Formulation 7
    1.0 mg/mL rFVIIa
    10 mM Histidine
    10 mM Glycylglycine
    50 mM Sodium chloride
    10 mM Calcium chloride
    50 µM N-(3-Bromobenzyl)-2-[3-(4-carbamimidoylphenyl)-ureido]-acetamide HCl
    pH=7.5
Formulation 8
    1.0 mg/mL rFVIIa
    10 mM Histidine
    10 mM Glycylglycine
    50 mM Sodium chloride
    10 mM Calcium chloride
    500 µM N-(3-Bromobenzyl)-2-[3-(4-carbamimidoylphenyl)-ureido]-acetamide HCl
    pH=7.5

The formulations were prepared by adding 10 mM histidine, 50 mM benzamidine (for formulations 2 and 6) and 50/500 µM N-(3-Bromobenzyl)-2-[3-(4-carbamimidoylphenyl)-ureido]-acetamide HCl (for formulation 3, 4 and 7,8 to a 1.0 mg/mL bulk solution of rFVIIa already containing glycylglycine, sodium chloride and calcium chloride in the above-mentioned concentrations. pH was finally adjusted to 6.5 and 7.5, respectively, with 1 M sodium hydroxide and 1 M hydrochloric acid.

The formulations were stored at a temperature of 5° C. and 30° C. and the analyses for Clot activity were performed at the time points shown in Table 6:

TABLE 6

Clot activity (IU/mL)

| | Storage time at 5° C. (months) | | | | |
|---|---|---|---|---|---|
| Formulation | 0 | 3 | 7 | 10 | 12 |
| 1 | 46.200 | 31.000 | <1.000 | Not analysed | Not analysed |
| 2 | 43.300 | 43.800 | 44.400 | 43.200 | 45.000 |
| 3 | 44.300 | 36.700 | 33.700 | * | 31.200 |
| 4 | 46.000 | 37.800 | 35.600 | * | 36.000 |
| 5 | 42.800 | 14.900 | 9.700 | Not analysed | Not analysed |
| 6 | 44.700 | 40.000 | 40.600 | 39.300 | 40.500 |
| 7 | 44.100 | 35.800 | 32.700 | 29.200 | * |
| 8 | 43.300 | 40.800 | 39.400 | * | 36.600 |

| | Storage time at 30° C. (months) | | |
|---|---|---|---|
| Formulation | 0 | 1 | 2 |
| 1 | 46.200 | 26.200 | 16.900 |
| 2 | 43.300 | 38.100 | 31.000 |
| 3 | 44.300 | 25.800 | 17.500 |
| 4 | 46.000 | 22.000 | 14.900 |
| 5 | 42.800 | 17.200 | 10.500 |
| 6 | 44.700 | 28.800 | 19.000 |
| 7 | 44.100 | 17.900 | 13.400 |
| 8 | 43.300 | 23.900 | 17.100 |

*unreliable result, not reported

Example 7

In order to investigate the effect of different stabilisers on the stability of rFVIIa the following formulations were prepared:
Formulation 1
    1.0 mg/mL rFVIIa
    10 mM Histidine
    10 mM Glycylglycine
    50 mM Sodium chloride
    10 mM Calcium chloride
    pH=6.5
Formulation 2
    1.0 mg/mL rFVIIa
    10 mM Histidine
    10 mM Glycylglycine
    50 mM Sodium chloride
    10 mM Calcium chloride
    5 mM p-amino-Benzamidine
    pH=6.5
Formulation 3
    1.0 mg/mL rFVIIa
    10 mM Histidine
    10 mM Glycylglycine
    50 mM Sodium chloride
    10 mM Calcium chloride
    0.05 mM S-2-[3-(4-Carbamimidoylphenyl)-ureido]-N-[1-(3-methoxyphenyl)-ethyl]-acetamide
    pH=6.5
Formulation 4
    1.0 mg/mL rFVIIa
    10 mM Histidine
    10 mM Glycylglycine
    50 mM Sodium chloride
    10 mM Calcium chloride 0.5 mM S-2-[3-(4-Carbamimidoylphenyl)-ureido]-N-[1-(3-methoxyphenyl)-ethyl]-acetamide
pH=6.5
Formulation 5
  1.0 mg/mL rFVIIa
  10 mM Histidine
  10 mM Glycylglycine
  50 mM Sodium chloride
  10 mM Calcium chloride
  pH=7.5
Formulation 6
  1.0 mg/mL rFVIIa
  10 mM Histidine
  10 mM Glycylglycine
  50 mM Sodium chloride
  10 mM Calcium chloride
  5 mM p-amino-Benzamidine
  pH=7.5
Formulation 7
  1.0 mg/mL rFVIIa
  10 mM Histidine
  10 mM Glycylglycine
  50 mM Sodium chloride
  10 mM Calcium chloride
  0.05 mM S-2-[3-(4-Carbamimidoylphenyl)-ureido]-N-[1-(3-methoxyphenyl)-ethyl]-acetamide
  pH=7.5
Formulation 8
  1.0 mg/mL rFVIIa
  10 mM Histidine
  10 mM Glycylglycine
  50 mM Sodium chloride
  10 mM Calcium chloride
  0.5 mM S-2-[3-(4-Carbamimidoylphenyl)-ureido]-N-[1-(3-methoxyphenyl)-ethyl]-acetamide
  pH=7.5

The formulations were prepared by adding 10 mM histidine, 5 mM p-amino-Benzamidine (for formulations 2 and 6) and 0.05/0.5 mM S-2-[3-(4-Carbamimidoylphenyl)-ureido]-N-[1-(3-methoxyphenyl)-ethyl]-acetamide (for formulations 3, 7 and 4, 8) to a 1.0 mg/mL bulk solution of rFVIIa already containing glycylglycine, sodium chloride and calcium chloride in the above-mentioned concentrations. pH was finally adjusted to 6.5 and 7.5, respectively, with 1 M sodium hydroxide and 1 M hydrochloric acid.

The formulations were stored at a temperature of 5° C. and the analyses for Clot activity (Table 7) and Heavy chain degradation (Table 8) were performed at the time points shown in the tables:

TABLE 7

| | Clot activity (IU/mL) | | | |
| --- | --- | --- | --- | --- |
| | Storage time at 5° C.(months) | | | |
| Formulation | 0 | 3 | 6 | 9 |
| 1 | 42.400 | 29.300 | 23.500 | 20.600 |
| 2 | 40.700 | 46.700 | 39.500 | 41.200 |
| 3 | 39.600 | 40.800 | 40.200 | 40.100 |
| 4 | 43.400 | 42.400 | 39.700 | 44.200 |
| 5 | 38.900 | 16.200 | 9.800 | Not analysed |
| 6 | 44.900 | 42.500 | 37.800 | 35.900 |
| 7 | 39.100 | 39.100 | 40.200 | 38.900 |
| 8 | 39.800 | 41.200 | 45.700 | 43.100 |

TABLE 7-continued

| | Clot activity (IU/mL) | | |
| --- | --- | --- | --- |
| | Storage time at 30° C.(months) | | |
| Formulation | 0 | 2 | 3 |
| 1 | 42.400 | 15.000 | 8.700 |
| 2 | 40.700 | 21.600 | 15.400 |
| 3 | 39.600 | 19.100 | 12.000 |
| 4 | 43.400 | 29.700 | 25.400 |
| 5 | 38.900 | 11.000 | 6.300 |
| 6 | 44.900 | 18.300 | 11.100 |
| 7 | 39.100 | 21.600 | 15.100 |
| 8 | 39.800 | 34.800 | 27.300 |

TABLE 8

| | Content of Heavy chain degradation (%) | | | |
| --- | --- | --- | --- | --- |
| | Storage time at 5° C.(months) | | | |
| Formulation | 0 | 1 | 3 | 6 |
| 1 | 12.9 | 23.6 | 38.0 | 51.1 |
| 2 | 12.1 | 12.5 | 13.4 | 15.2 |
| 3 | 12.2 | 13.0 | 15.0 | 18.5 |
| 4 | 12.1 | 11.5 | 10.9 | 12.0 |
| 5 | 16.9 | 54.0 | 71.5 | 76.7 |
| 6 | 12.7 | 16.7 | 22.0 | 29.1 |
| 7 | 12.4 | 13.3 | 13.8 | 17.2 |
| 8 | 11.9 | 11.3 | 11.3 | 11.7 |
| | Storage time at 30° C.(months) | | | |
| Formulation | 0 | 1 | 2 | 3 |
| 1 | 12.9 | 23.3 | 26.3 | 29.0 |
| 2 | 12.1 | 20.2 | 23.2 | 26.7 |
| 3 | 12.2 | 20.3 | 23.8 | 25.9 |
| 4 | 12.1 | 14.8 | 16.4 | 18.6 |
| 5 | 16.9 | 41.1 | 47.7 | 49.2 |
| 6 | 12.7 | 34.8 | 41.5 | 46.3 |
| 7 | 12.4 | 32.3 | 39.1 | 43.4 |
| 8 | 11.9 | 14.5 | 16.3 | 18.1 |

Example 8

In order to investigate the effect of S-2-[3-(4-Carbamimidoylphenyl)-ureido]-N-[1-(3-methoxyphenyl)-ethyl]-acetamide on the stability of rFVIIa the following formulations were prepared:
Formulation 1
  1.0 mg/mL rFVIIa
  50 mM Sodium chloride
  10 mM Calcium chloride
  10 mM Glycylglycine
  20 mM Histidine
  0.5 mg/mL Methionine
  5 mM S-2-[3-(4-Carbamimidoylphenyl)-ureido]-N-[1-(3-methoxyphenyl)-ethyl]-acetamide
  pH=6.0
Formulation 2
  1.0 mg/mL rFVIIa
  50 mM Sodium chloride
  10 mM Calcium chloride
  10 mM Glycylglycine
  20 mM Histidine
  0.5 mg/mL Methionine 5 mM S-2-[3-(4-Carbamimidoylphenyl)-ureido]-N-[1-(3-methoxyphenyl)-ethyl]-acetamide
pH=6.5
Formulation 3
1.0 mg/mL rFVIIa
50 mM Sodium chloride
10 mM Calcium chloride
10 mM Glycylglycine
20 mM Histidine
0.5 mg/mL Methionine
5 mM S-2-[3-(4-Carbamimidoylphenyl)-ureido]-N-[1-(3-methoxyphenyl)-ethyl]-acetamide
pH=7.5

The formulations were prepared by adding 20 mM histidine, 5 mM S-2-[3-(4-Carbamimidoylphenyl)-ureido]-N-[1-(3-methoxyphenyl)-ethyl]-acetamide and 0.5 mg/mL Methionine to a solution of rFVIIa already containing glycylglycine, sodium chloride and calcium chloride in the above-mentioned concentrations. pH was finally adjusted to 6.0, 6.5 and 7.5, respectively, with 1 M sodium hydroxide/hydrochloric acid.

The formulations were stored at a temperature of 25° C. and the analyses for Clot activity (Table 9) and Heavy chain degradation (Table 10) were performed at the time points shown in the tables:

TABLE 9

| | Clot activity (IU/mL) | | | |
|---|---|---|---|---|
| | Storage time at 5° C. (months) | | | Storage time at 25° C. (months) |
| Formulation | 0 | 3 | 6 | 3 |
| 1 | 38.400 | 45.500 | 41.700 | 38.500 |
| 2 | 39.800 | 41.200 | 37.800 | 42.400 |
| 3 | 42.400 | 43.000 | 39.500 | 39.900 |

The reference formulations without S-2-[3-(4-Carbamimidoylphenyl)-ureido]-N-[1-(3-methoxyphenyl)-ethyl]-acetamide shows the following Clot activity.

TABLE 10

| | Clot activity (IU/mL) for reference solutions | | | |
|---|---|---|---|---|
| Reference | Storage time at 5° C. (months) | | | Storage time at 25° C. (months) |
| Formulation | 0 | 1 | 3 | 3 |
| 1 | 38.400* | 44.400 | 21.300 | 4.400 |
| 2 | 39.800* | 40.100 | 15.400 | 2.500 |
| 3 | 42.400* | 26.400 | 7.700 | <1.000 |

*The time zero results for the reference solutions are not available, for this reason the corresponding values for the solutions containing the inhibitor substance has been listed.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The invention claimed is:

1. A method for treating a Factor VII-responsive syndrome comprising administering to a subject in need thereof an effective amount of a liquid, aqueous, and pharmaceutically acceptable composition, the composition comprising
   (i) at least 0.01 mg/mL of a Factor VII polypeptide that exhibits substantially the same or improved biological activity as compared to wild type Factor VII;
   (ii) a buffering agent suitable for keeping pH of the composition in the range of about 4 to about 9; and
   (iii) a stabilizing composition comprising a benzamidine compound according to the formula —$C_6H_4$—C(=N—$Z^1$—$R^1$)—NH—$Z^2$—$R^2$, wherein
      (a) $C_6H_4$ denotes a substituted benzene ring, and
      (b) $Z^1$ and $Z^2$ independently are selected from the group consisting of —O—, —S—, —$NR^{H-}$ and a single bond, where $R^H$ is selected from the group consisting of hydrogen, $C_{1-4}$-alkyl, aryl and arylmethyl, and $R^1$ and $R^2$ independently are selected from the group consisting of hydrogen, optionally substituted $C_{1-6}$-alkyl, optionally substituted $C_{2-6}$-alkenyl, optionally substituted aryl, optionally substituted heterocyclyl, wherein
      —C=N—$Z^1$—$R^1$ optionally forms part of a heterocyclic ring,
      —C—NH—$Z^2$—$R^2$ optionally forms part of a heterocyclic ring, or
      —C(=N—$Z^1$—$R^1$)—NH-$Z^2$—$R^2$ optionally forms a heterocyclic ring wherein $Z^1$—$R^1$—$R^2$—$Z^2$— is a biradical.

2. The method of claim 1, wherein the Factor VII-responsive syndrome is a bleeding disorder.

3. The method of claim 1, wherein the Factor VII-responsive syndrome is a disorder caused by a clotting factor deficiency.

4. The method of claim 1, wherein the Factor VII-responsive syndrome is haemophilia A.

5. The method of claim 1, wherein the Factor VII-responsive syndrome is haemophilia B.

6. The method of claim 1, wherein the Factor VII-responsive syndrome is a disorder caused by Factor VII deficiency.

7. The method of claim 1, wherein the Factor VII-responsive syndrome is thrombocytopenia.

8. The method of claim 1, wherein the Factor VII-responsive syndrome is von Willebrand's disease.

9. The method of claim 1, wherein the Factor VII-responsive syndrome is a disorder caused by a clotting factor inhibitor.

* * * * *